(12) United States Patent
Bublewitz et al.

(10) Patent No.: US 10,413,384 B2
(45) Date of Patent: Sep. 17, 2019

(54) CONTAINER FOR STORING AND DISPENSING AT LEAST ONE COMPONENT AND METHOD THEREFOR

(71) Applicant: Kettenbach GMBH & Co. KG, Eschenburg (DE)

(72) Inventors: Alexander Bublewitz, Herborn (DE); Jens-Peter Reber, Meinerzhagen (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 0 days.

(21) Appl. No.: 15/739,966

(22) PCT Filed: Jun. 28, 2016

(86) PCT No.: PCT/EP2016/065026
§ 371 (c)(1),
(2) Date: Dec. 26, 2017

(87) PCT Pub. No.: WO2017/001412
PCT Pub. Date: Jan. 5, 2017

(65) Prior Publication Data
US 2018/0177569 A1  Jun. 28, 2018

(30) Foreign Application Priority Data
Jun. 29, 2015 (DE) .................. 10 2015 110 442

(51) Int. Cl.
*B05C 17/005* (2006.01)
*A61C 5/64* (2017.01)
(Continued)

(52) U.S. Cl.
CPC .............. *A61C 5/64* (2017.02); *A61M 35/003* (2013.01); *B01F 5/0615* (2013.01);
(Continued)

(58) Field of Classification Search
CPC ........ B05C 17/00553; B05C 17/00516; B05C 17/00506; B05C 17/00509;
(Continued)

(56) References Cited

U.S. PATENT DOCUMENTS 4,432,469 A * 2/1984 Eble ..................... B01F 5/0077
222/134
5,052,927 A  10/1991 Discko, Jr.
(Continued)

FOREIGN PATENT DOCUMENTS

DE  29709383 U1  8/1998
DE  69523561 T2  4/2002
(Continued)

OTHER PUBLICATIONS

English Translation of Abstract of German Patent Application No. DE 102007044983 dated Dec. 22, 2017.
(Continued)

*Primary Examiner* — Charles Cheyney
(74) *Attorney, Agent, or Firm* — McDonnell Boehnen Hulbert & Berghoff LLP

(57) ABSTRACT

The invention relates to a container (1) for storing and discharging at least one component with at least one chamber (4, 4a, 4b), which is sealed on a first side by a plug (9), and with one applicator (5) attached on the first side. A flow connection between the at least one chamber (4, 4a, 4b) and the side of the applicator (5) facing away from the at least one chamber (4, 4a, 4b) is opened by a relative rotational movement of the applicator (5) to the container (1) and a subsequent axial relative movement of the plug (9) to the container (1) and the applicator (5), in particular due to pressure of the at least one component on the plug (9). Furthermore, the invention relates to a method for storing and discharging at least one component.

13 Claims, 17 Drawing Sheets

Figure 1:
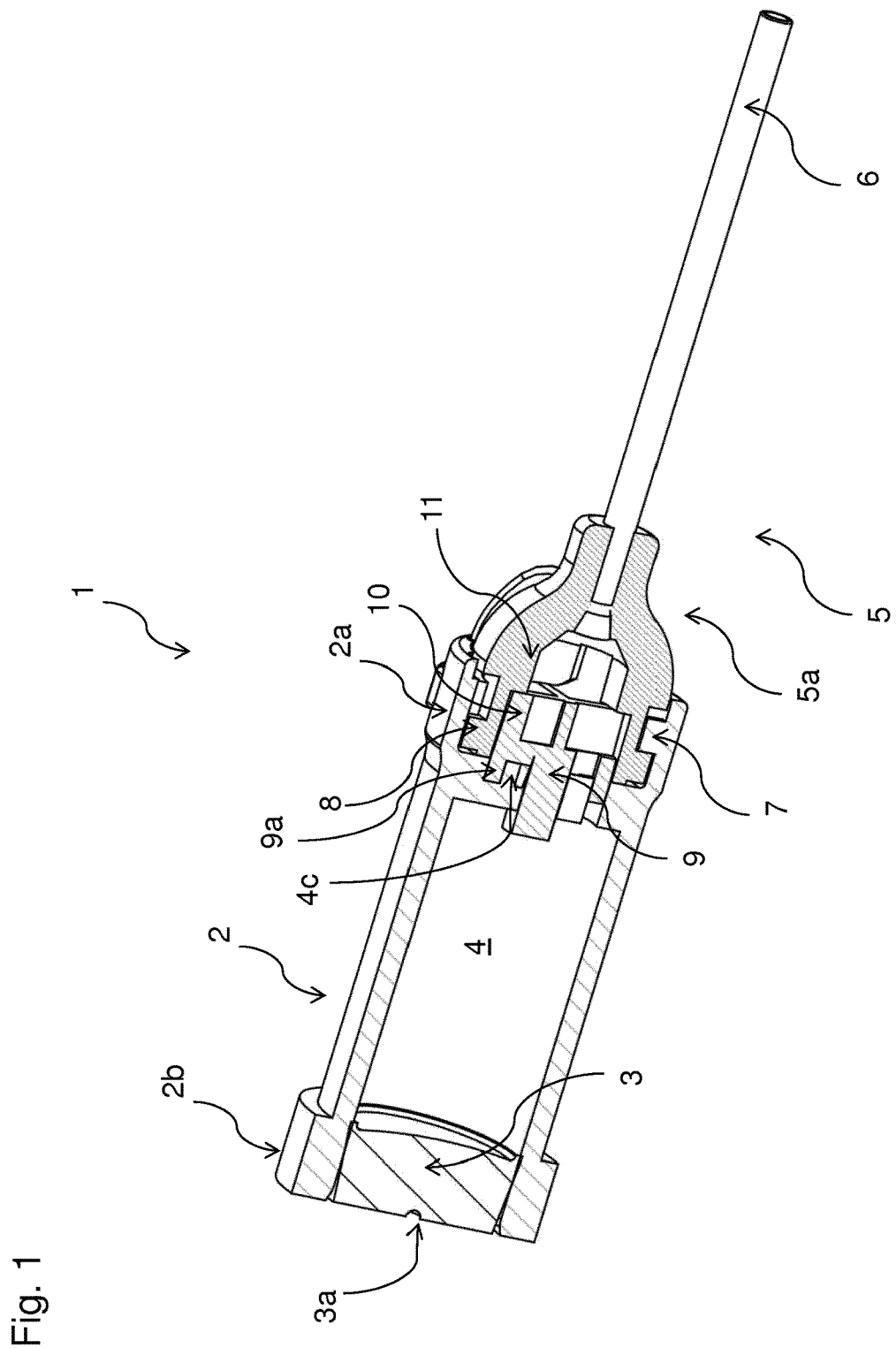

(51) Int. Cl.
*A61M 35/00* (2006.01)
*B01F 5/06* (2006.01)
*B01F 15/02* (2006.01)

(52) U.S. Cl.
CPC ...... *B01F 15/0215* (2013.01); *B01F 15/0237* (2013.01); *B05C 17/00509* (2013.01); *B05C 17/00559* (2013.01); *B01F 2215/0039* (2013.01); *B05C 17/00576* (2013.01)

(58) Field of Classification Search
CPC .......... B05C 17/00593; B05C 17/0146; B05C 17/00559; B05C 17/00576; A61C 5/62; A61C 5/64; A61M 35/003; B01F 15/0215; B01F 15/0237
USPC ...... 222/137, 135, 145.6, 145.1, 525, 145.5, 222/459
See application file for complete search history.

(56) References Cited

U.S. PATENT DOCUMENTS

| | | | |
|---|---|---|---|
| 6,457,101 B1 | 9/2002 | Bauman et al. | |
| 6,769,564 B2 | 8/2004 | Prestele | |
| 6,769,574 B1* | 8/2004 | Keller | B05C 17/00509 222/137 |
| 7,694,853 B2 | 4/2010 | Keller | |
| 7,882,983 B2* | 2/2011 | Reidt | A61C 9/0026 222/137 |
| 7,938,296 B2* | 5/2011 | Keller | B05C 17/00509 222/135 |
| 8,033,429 B2 | 10/2011 | Keller | |
| 8,177,099 B2 | 5/2012 | Suchan et al. | |
| 8,602,775 B2 | 12/2013 | Pauser | |
| 8,616,879 B2 | 12/2013 | Dubey et al. | |
| 8,684,233 B2* | 4/2014 | Nishio | B65D 81/3288 222/1 |
| 8,733,593 B2* | 5/2014 | Brem | B65D 83/0072 222/137 |
| 9,138,772 B2* | 9/2015 | Pappalardo | B05C 17/00553 |
| 9,617,062 B2* | 4/2017 | Leue | B05C 17/00506 |
| 2002/0052579 A1* | 5/2002 | Sogaro | A45D 19/02 604/218 |
| 2006/0227653 A1* | 10/2006 | Keller | A61B 17/00491 366/139 |
| 2007/0175921 A1 | 8/2007 | Keller | |
| 2008/0029542 A1* | 2/2008 | Keller | B05C 17/00509 222/145.5 |
| 2008/0195082 A1 | 8/2008 | Pauser et al. | |
| 2009/0308891 A1 | 12/2009 | Bublewitz et al. | |
| 2011/0198370 A1* | 8/2011 | Ho | B01F 5/0615 222/137 |
| 2012/0228329 A1 | 9/2012 | Staub | |

FOREIGN PATENT DOCUMENTS

| | | |
|---|---|---|
| DE | 20106406 U1 | 8/2002 |
| DE | 102005041961 A1 | 3/2007 |
| DE | 102005041962 B3 | 3/2007 |
| DE | 202006015457 U1 | 2/2008 |
| DE | 102007044983 A1 | 4/2009 |
| DE | 102012024408 A1 | 6/2013 |
| EP | 1125641 B1 | 5/2003 |
| EP | 1389448 A1 | 2/2004 |
| EP | 1426017 A2 | 6/2004 |
| EP | 1656215 B1 | 9/2010 |
| EP | 1758685 B1 | 11/2011 |
| EP | 2190592 B1 | 2/2012 |
| WO | 2005016783 A1 | 2/2005 |
| WO | 2005021394 A2 | 3/2005 |
| WO | 2006005213 A1 | 1/2006 |
| WO | 2006132932 A1 | 12/2006 |
| WO | 2009063962 A1 | 5/2009 |
| WO | 2011041917 A1 | 4/2011 |

OTHER PUBLICATIONS

English Translation of Abstract of German Patent Application No. DE 102012024408 dated Dec. 22, 2017.
English Translation of Abstract of WO 20091063962 dated Dec. 22, 2017.
Notification of Transmittal of Translation of the International Preliminary Report on Patentability dated Jan. 4, 2018.

* cited by examiner

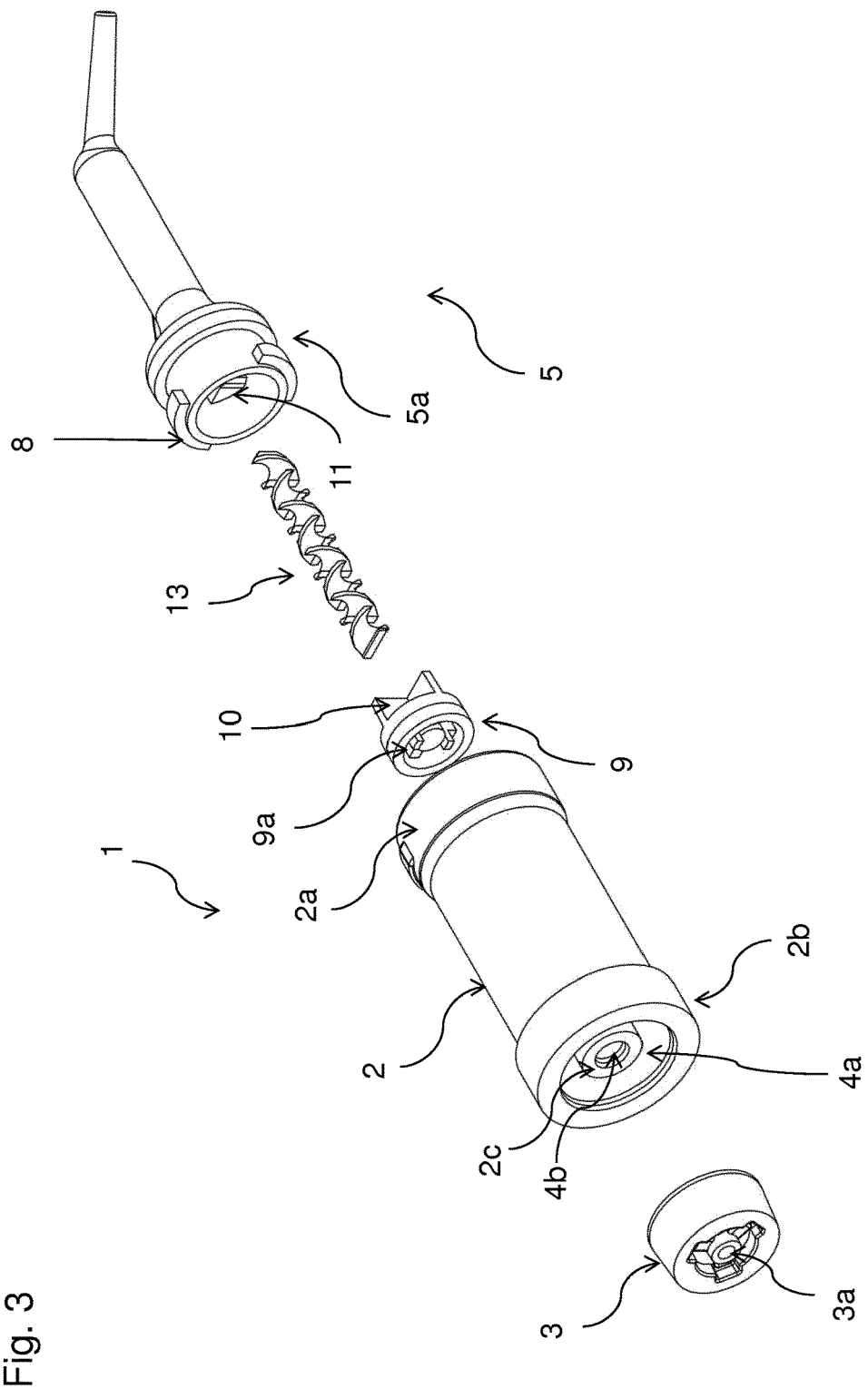

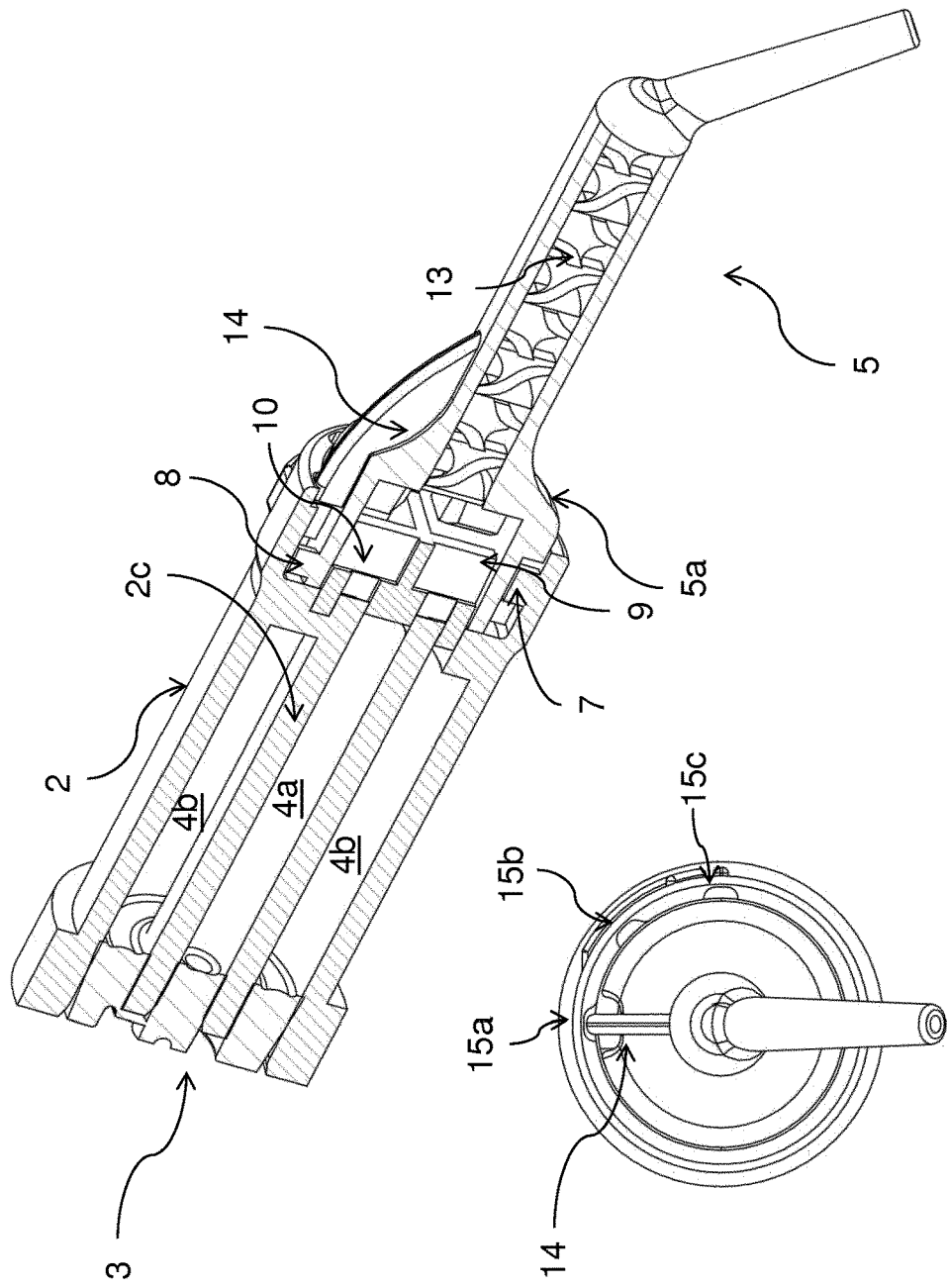

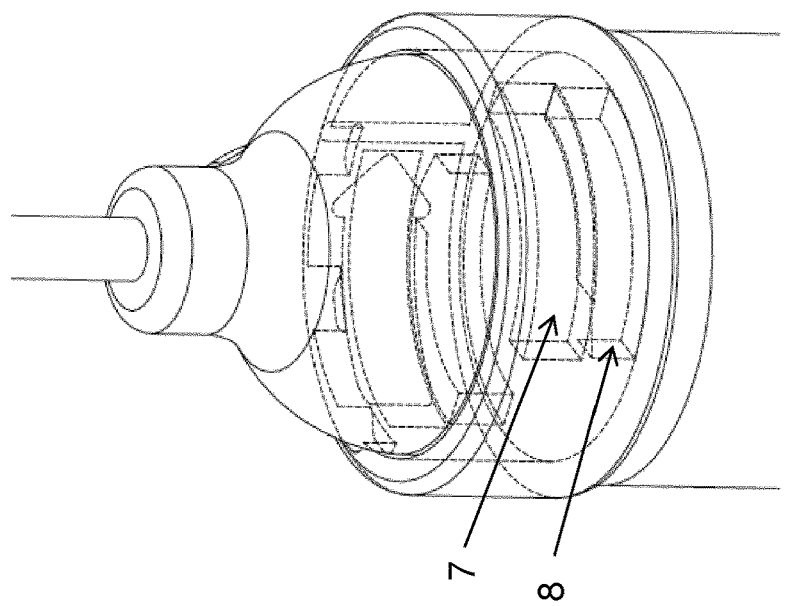
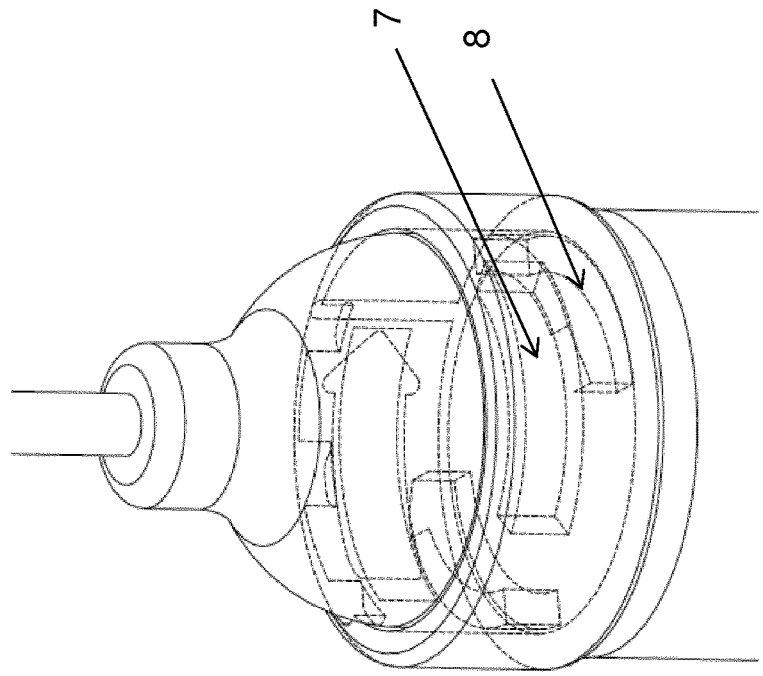

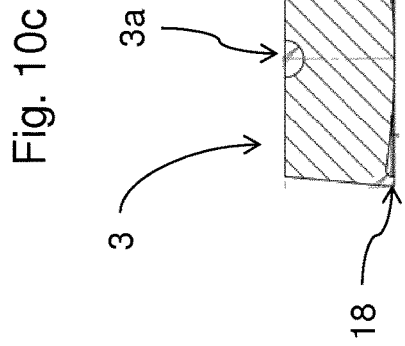
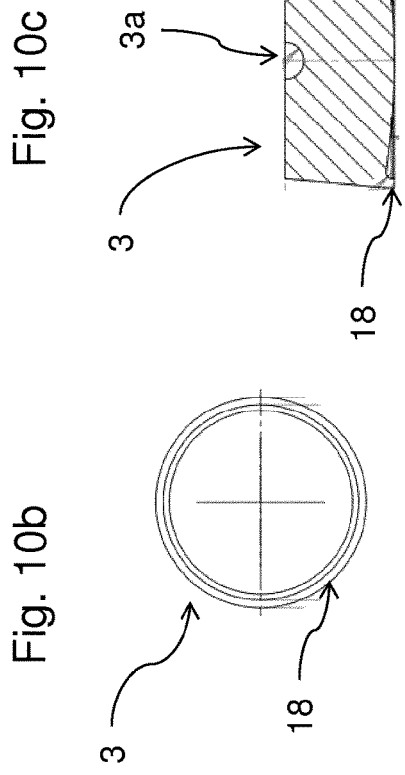
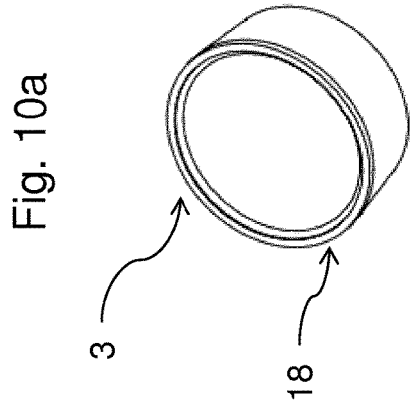
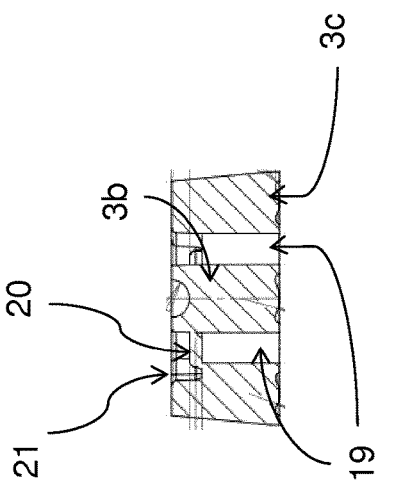
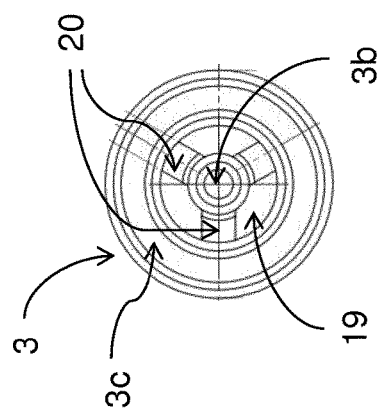
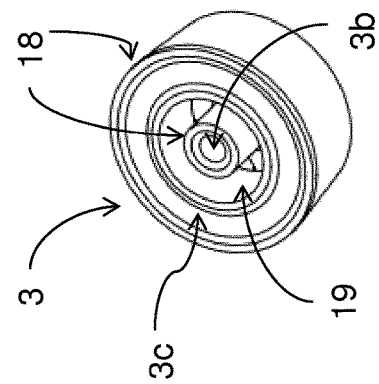

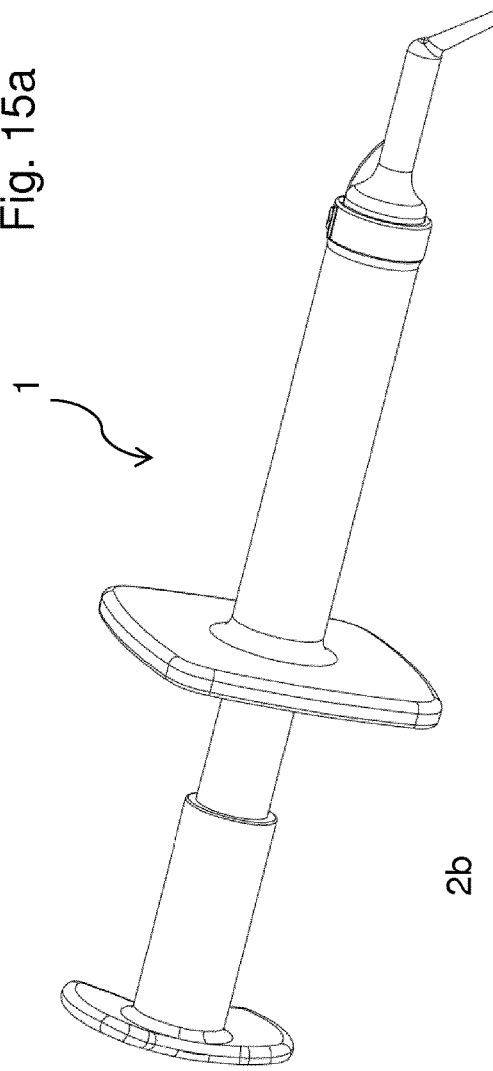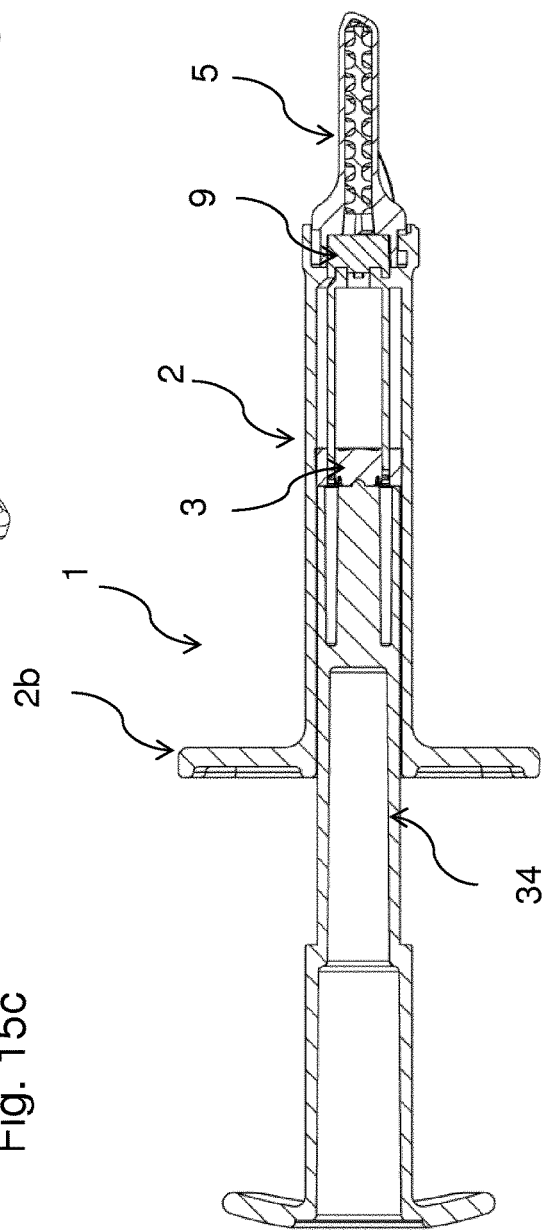

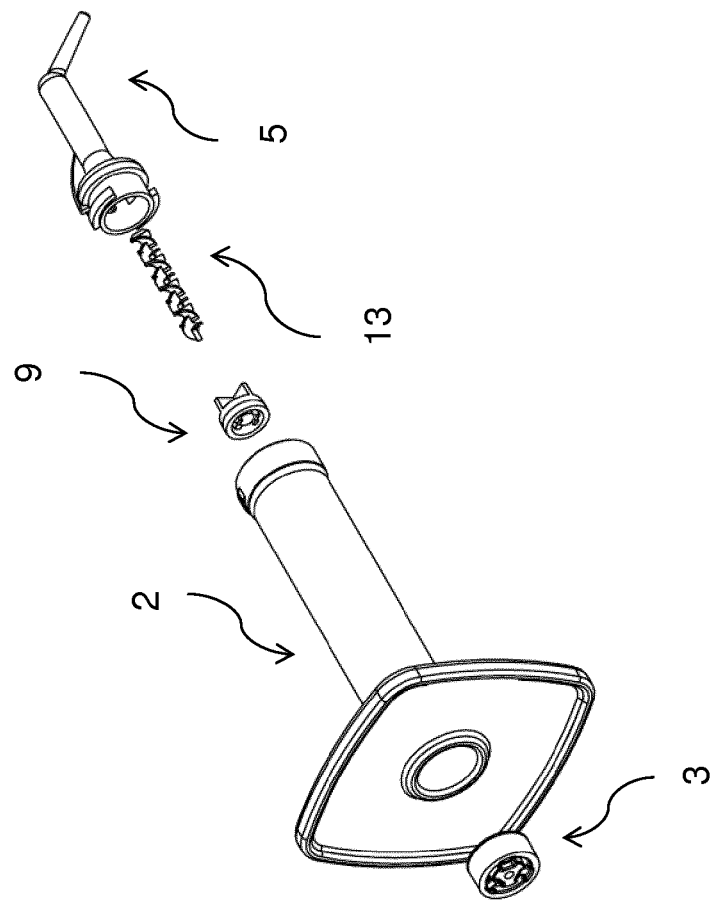
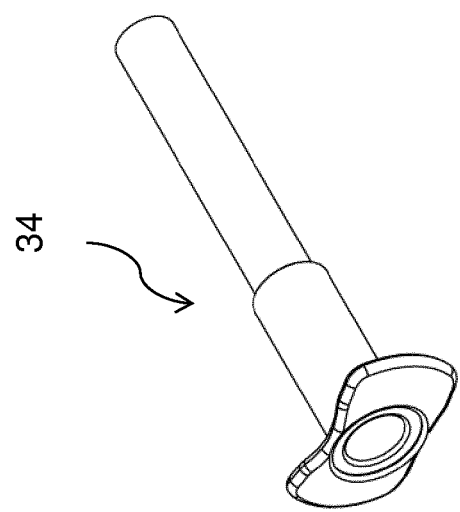
Fig. 15b

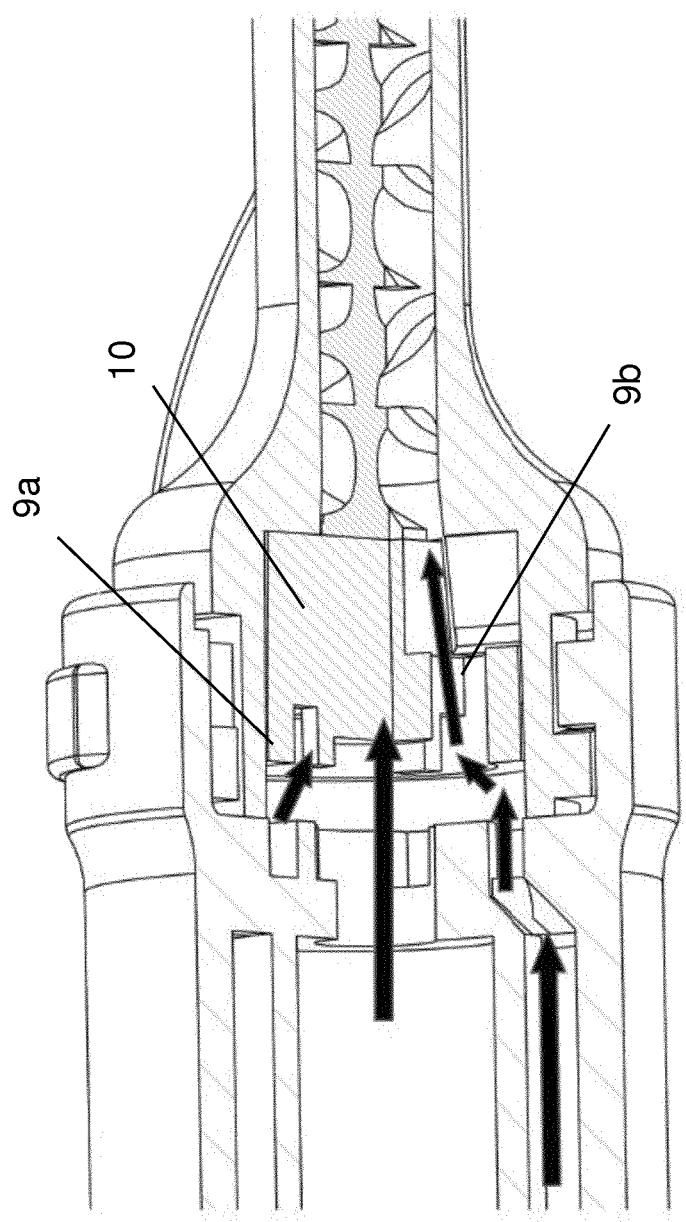

CONTAINER FOR STORING AND DISPENSING AT LEAST ONE COMPONENT AND METHOD THEREFOR

CROSS REFERENCE TO RELATED APPLICATIONS

The present application is a U.S. National Phase Application pursuant to 35 U.S.C. § 371 of International Application No. PCT/EP2016/065026 filed Jun. 28, 2016, which claims priority to German Patent Application No. 10 2015 110 442.3 filed Jun. 29, 2015. The entire disclosure contents of these applications are hereby incorporated by reference into the present application.

The invention relates to a container for storage and discharge of at least one component with at least one chamber, which is sealed by a plug at a first (distal) side and by a movable piston at the opposite (proximal) side, and with an applicator being attached at the first side, wherein the plug is movable relative to the chamber from a storage position, in which the flow connection between the chamber and the applicator is interrupted by the plug, to an output position, in which the chamber is in flow connection with the applicator.

Such cartridges for connection with a mixer as applicator are in known from DE 10 2005 041 961 B4 and DE 10 2005 041 962 B4.

From EP 1 758 685 B1 a generic syringe for discharge of multicomponent pastes is known. The syringe comprises two concentrically arranged chambers, which are sealed by a plug. For discharging the components from the chambers a piston assembly comprising multiple pistons is used. If the piston assembly is displaced for discharging the components, the plug automatically opens by the generated internal pressure of the components by being displaced in the direction of the discharge opening and opening a discharge channel for each component. Such an opening mechanism for a sealing plug caused by the internal pressure of the components is also described in WO 2006/132932 A1 and EP 2 190 592 B1.

EP 1 656 215 B2 describes a single dose syringe for a multicomponent material. At the cartridge of the syringe a mixer housing is arranged, wherein the mixer housing can be affixed on the cartridge via a bayonet lock. The mixing helix can be integrally connected to a sealing plug, wherein the mixing helix is displaced with the sealing plug by the internal pressure of the components in the direction of the opening and thus enables a discharge of the components. WO 2005/016783 A1 also discloses a sealing plug for two chambers, which is affixed to a mixing helix and, together with the latter, can be displaced by the internal pressure of the components in order to enable discharge of the components.

U.S. Pat. No. 8,616,879 B2 discloses a capsule for storing and subsequently discharging reactive or caustic materials. To open the capsule a tear-off attachment is removed. Subsequently, a sealing cap or a metal cannula can be placed on the capsule. A suitable applicator gun for such a capsule is described in U.S. Pat. No. 8,602,775 B2.

U.S. Pat. No. 5,052,927 describes a syringe and single-use capsule having a discharge cannula for discharging dental material. The discharge cannula is rotatably affixed to the single-use capsule.

DE 20 2006 015 457 U1 describes a multicomponent cartridge, which is formed integrally with a mixing element and with a mixer housing defined via a snap connection to the cartridge. The components to be discharged are stored in two chambers, which have discharge openings closed by a sealing plug, which is connected to the inside of the connection area of the mixer. To discharge the components, the mixer housing together with the plug is lifted axially from the cartridge, whereby the discharge openings are opened.

U.S. Pat. No. 6,547,101 B also discloses a sealing plug for a two-component cartridge which can be displaced from a position sealing the chambers of the cartridge into a position opening the chambers by an axial movement relative to the chambers of a cartridge and an applicator. The plug must be pushed opposite to the delivery direction of the components into the chambers. A similar opening mechanism is also disclosed by EP 1 389 448 A1 and EP 1 426 017 A2.

The single-use discharge device disclosed in WO 2006/005213 A1 has a mixer which can be affixed on a cartridge, whose axial displacement or rotation opens a discharge channel of the cartridge by opening a passage channel or pulling a sealing plug out of the discharge channel. A combination of both types of movement of the mixer for opening the discharge channel is described. In this case, the mixer is guided on a thread-like inclination of the cartridge, which converts a rotational movement of the mixer into a simultaneously occurring axial displacement. Said axial displacement of the mixer in turn removes a plug from the discharge channel of the cartridge so that it is opened. WO 2011/041917 A1 also describes such an opening system for discharge channels, wherein a bayonet connection having inclined ramps for generating an axial stroke is used.

US 2011/0198370 A1 describes a sealing plug which is pushed through when a mixer connected to the cartridge by means of a thread is screwed tightly onto the cartridge.

DE 297 09 383 U1 discloses a discharge device with an outlet nozzle arranged on a cartridge, which has lateral discharge openings. Further, a sealing sleeve is provided, which opens the lateral discharge openings when placing a mixer on the cartridge and closes when removing the mixer from the cartridge. This function is achieved by inclined engagement slots and drivers on the sealing sleeve.

Such containers are also known as so-called preloaded tips (PLT) for discharging single and multicomponent dental composites. These are used in particular for particularly air- and/or light-sensitive and/or corrosive and/or caustic components which can and/or should be used only once. The containers must achieve a high sealing and thus a good storage stability of the components and allow easy and safe discharge of the components. A disadvantage of some known solutions is that before using the container, the applicator has to be mounted and, if necessary, a closure has to be disassembled. In addition, in some known containers, the plug closing the chamber(s) can be inadvertently opened, for example by fluctuations in the internal pressure.

US 2012/0 228 329 A1 A describes a discharge device with a multicomponent cartridge, an attachable mixer and a union nut for fixing the mixer on the cartridge. The mixer has closure elements that close the discharge channels of the cartridge and can open these by axial displacement of the mixer in the discharge direction. Said axial displacement of the mixer is achieved by turning the cap nut.

US 2008/0 195 082 A1 discloses a dispensing syringe having concentrically arranged chambers which can be closed in sealing plug. The sealing plug can be displaced in the axial direction during discharge and has a bypass channel, so that the respective material from the chambers can be guided into a mixer.

DE 201 06 406 U1 discloses a seal for a two-component cartridge with a sealing plug with two sealing bolts, which are insertable into the discharge openings of the respective chamber and thus close them. The sealing plug can be fixed to the cartridge with a union nut and is connected to the union nut via a detachable snap connection.

DE 695 23 561 T2 describes a bayonet connection device for fastening an accessory, for example a mixer or a sealing plug, to a multi-component cartridge or dispensing device.

US 2007/0175 921 A1 discloses a sealing plug which closes two chambers and, after a rotary movement of an applicator, can be displaced axially by the internal pressure during discharge of the components and thereby opening a discharge channel. This is achieved by arranging two projections on the mixer such that an axial displacement of the plug is prevented in the closure position. If the mixer is rotated by 90° and reaches a discharge position, the projections of the mixer can be received by correspondingly formed recesses of the plug and thus allow an axial displacement of the plug and thus opening of the flow channel, so that the components stored in the chambers are discharged.

The object of the present invention is provide a container of the type mentioned above, which enables particularly safe and tight storage of the components, unaffected by external conditions, such as temperature or pressure fluctuations, mechanical transport loads (shaking, falling, etc.) and at the same time a high level of user friendliness. The container is also intended to allow fault-avoiding use by preventing inadvertent activation and allowing active provision of the container when the content of the container is still tightly sealed.

This object is solved by a container having the features of claim 1. A core idea of the invention lies in a two-stage opening process of the container, wherein in a first step, in particular by a relative rotation of the applicator to the container, a provision state is achieved and in a second step, in particular by an axial movement of the plug relative to the container and/or the applicator, a flow connection between the at least one chamber and the applicator is established. While still in the provision state, the at least one chamber is still sealed by the plug, but the plug maybe displaced at any time, e.g. by the internal pressure of the component in the chamber, to establish the flow connection. In contrast, before the first step, i.e. in a transport or storage state of the container, an axial movement of the plug—and thus the opening of a flow connection between the at least one chamber and the applicator—is prevented. Thus, inadvertent opening of the container, e.g. due to temperature or pressure fluctuations or mechanical transport loads, in its transport or storage state actively prevented.

In other words, the container is provided in a transport or storage state in which the container is securely sealed, and can be transferred by rotation of the applicator relative to the container in a provision state, in which the container is still sealed, but without further steps, it can be fully opened solely by the pressure exerted on the components during discharging of the same, which causes axial displacement of the plug, so that the components can be discharged from the applicator.

The invention is characterized essentially by the fact that the plug sealing the chamber(s) is held displaceably in a storage position of an applicator, while in a provision position of the applicator the plug can be displaced axially from its storage position, in which a flow connection between the chamber and the applicator is interrupted by the plug, in its dispensing position, in which the chamber is in fluid communication with the applicator, and that the applicator can be transferred from the storage position by rotation in the provision position. In other words, the invention is thus based on the idea that the plug is held in its storage position until the applicator is moved from the storage position to the provision position, for example by a rotary movement of the applicator. Only in this provision position of the applicator the plug can be moved into its dispensing position in order to open flow channels for the components stored in the container. This will prevent inadvertent opening of the container, e.g. during transport and/or storage and even after the applicator is transferred to the provision position the container is still sealed by the plug, but can be opened at any time by a movement of the plug. The applicator thus acts as a transportation lock for the plug. Despite this improved security, compared to known containers, during transport and/or storage, the container is quickly and without elaborate assembly steps ready for use by only transferring the pre-assembled applicator from the delivery state of the container to the provision position. A rotational movement, which transfers the applicator from its storage position to the provision position, is, as viewed from outside by a user, a relative movement in the circumferential direction between applicator and container, however, relevant for the opening of the container after releasing the plug (i.e. its discharging position) is an axial relative movement between the applicator and the plug.

In the storage position of the plug flow communication between the chamber and the applicator is interrupted by the plug, while in the discharging position of the plug the chamber is in flow communication with the applicator. In order to prevent any displacement of the plug in the storage position, the plug has a first locking element and the applicator has a second locking element, which are aligned in the storage position, such that any displacement of the plug is prevented.

In the storage position the plug is not located within the chamber(s), but is received in an e.g. annular space of the container. However, the plug has sealing means which block fluid communication between the chamber and the applicator when the plug is in the storage position. These sealing means may comprise peripheral and/or frontal proximal seals of the e.g. substantially annular plug and/or at least one proximal projection, which seal a discharging passage of the respective chamber.

With the invention, it is thus possible to prepare the container, in particular by rotating the applicator into the provision position for discharging the at least one component, without the container already being opened and the component stored therein already exposed to environmental influences, for example air, which is due to the fact the plug has not yet moved to its discharge position. In other words, the provision position of the applicator and the discharging position of the plug are decoupled from each other, i.e. are insofar independent from each other, so that the plug does not have to be in its discharging position in the provision position of the applicator. However, the plug can only be moved to its discharging position when the applicator has already been rotated to its provision position. Thus, a preparatory opening of the container, for example by an assistant of a dentist in charge, is possible, without contamination of the at least one component even for subsequent prolonged non-use of the container, e.g. during a treatment waiting time.

A container according to the invention can be designed as a so-called one-component system with a single chamber and as so-called multi-component system and with a plurality of chambers. In particular, two-component systems comprising two substances typically to be mixed are frequently used. In this case, the chambers for receiving the two components may be arranged as cylinders next and parallel to each other, e.g. semicircular or into one another, e.g. concentric.

The applicator used may be a mixer, an optionally curved cannula, in particular a metal cannula, a brush or a sponge. A mixer with a curved cannula or metal cannula is preferred for multi-component systems, while simpler applicators, such as a cannula, are preferred for single-component systems.

Metal cannulas are used in particular for discharging e.g. highly viscous retraction pastes or thin-viscous flowable dental filling composites or fast-curing materials, in particular there are handling advantages for the user, since the metal needle is individually flexible for the respective oral situation, and since they are often mechanically stable and are returnable flexible. Due to the increased stability compared to plastic materials, the metal needles can be formed with a higher inner diameter with the same outer diameter, which is particularly advantageous for fast-curing materials, since clogging of the cannula is prevented or at least delayed or the discharge force is reduced.

Especially with corrosive and/or caustic materials, e.g. retraction pastes, etching gels, cements and adhesives, corrosion of the factory mounted metal needles regularly occurs. This problem is solved with the present invention, since the sealing effect of the plug caused by the cooperation of the first and second locking elements is so high that no corrosion occurs even in the manufacturer factory preassembled metal needles after prolonged storage.

The container according to the invention is preferably insertable into a conventional dispensing gun (for example a gun from Centrix or from Ronvig-Dental). To fix the container in the dispensing gun the container has a suitably designed retaining section. If the container, for example a capsule, is inserted in the dispensing gun, the at least one component can be discharged by actuating the plunger of the dispensing gun when the applicator is in the ready position and the plug is in the dispensing position.

It is preferred that the plug is displaceable by the internal pressure of the at least one component into the discharging position of the plug, provided that the applicator is in the provision position. Accordingly, an intuitive, automatic opening of the container, for example by actuation of the dispensing gun, is possible, wherein the at least one component is pressed in the direction of the applicator and thereby displaces the plug into the discharging position. Thereby, it is possible that after the rotation of the applicator relative to the container in its provision position, the user merely has to actuate the dispensing gun to discharge the components while at the same time contamination of the components prior to the actual discharging of the at least one component is prevented.

The second (proximal) end of the at least one chamber facing away from the applicator is preferably sealed by a piston on which a plunger of a dispensing gun can engage in order to discharge the at least one component by displacing the piston. Alternatively, it is possible to seal the chamber at the proximal end with a sealing foil, which can be pierced by a piston, in particular with a piston rod, when the at least one component is discharged. In a further alternative, the chamber may be completely sealed at its proximal end, wherein the at least one component is discharged e.g. by gas pressure.

In a preferred variant, the applicator is axially fixed both in the storage position and in the provision position, i.e. the applicator is not axially displaceable relative to the chamber. This does not exclude an axial movement component while the applicator is being transferred from the stored position to the provision position. Since the applicator is axially fixed in the storage position, inadvertent opening of the plug in the storage position by displacement of the applicator is prevented. Pressure and/or temperature fluctuations as well as mechanical loads occurring during storage and/or transport, for example vibrations or jarring movements, do not lead to an inadvertent release of the plug and thus not to a discharge of the components. If the applicator is not axially displaceable even in the provision position, high dispensing pressures can be applied e.g. by the dispensing gun.

It is further preferred that the applicator is rotatable relative to the chamber from a mounting position, in which the applicator is axially attachable to the container, to the storage position and to the provision position. Preferably, the direction of rotation is predefined so that the applicator is rotatable from the mounting position to the storage position and from the storage position to the provision position. Each angle to be rotated between the individual positions may be e.g. about 30 to 120° and thus on total of about 60 to 240°, preferably 30 to 90° and thus on total of 60 to 180° and more preferably 45 to 60° and thus on total of 90 to 120°. Preferably, the rotation is in each case by 45°. The mounting position is, e.g. during assembly prior to delivery to the user, the position in which the applicator is connected to the container. The connection between the applicator and the container can be designed, so that so that the applicator cannot be moved or not be moved non-destructively from the storage position to the mounting position. Thus, the applicator is in its delivery state to a user, i.e. in its storage position, captively secured on the container.

It is particularly useful to provide a receptacle for the applicator at the container, which has at least one radially inwardly directed bayonet projection. In this case, the applicator has a connection section which can be inserted into the receptacle and has at least one bayonet projection pointing radially outwards. In order to avoid tilting of the applicator, preferably two, three or more, bayonet projections are provided in each case. The bayonet projections are arranged relative to each other such that they allow in the mounting position, an attachment of the applicator to the container. If the applicator is rotated into the storage position, the corresponding bayonet projections of the connection section of the applicator and the receptacle of the container at least partially overlap, i.e. engage. Overlapping of the corresponding bayonet projections in the provision position, can prevent any axial displacement of the applicator. Preferably, the overlapping or engaging surface of the bayonet projections is greater in the provision position than in the storage position. It is preferred that the corresponding bayonet projections completely overlap with each other in the provision position, provided that the bayonet projections of applicator and container have the same length.

If the bayonet projections in the receptacle and/or the connection section have different lengths, a complete overlap or engagement, for example of the shorter, bayonet projection is preferred in the provision position. As an alternative to the applicator which can be inserted into the receptacle of the container, the applicator can have a receptacle into which the container can be inserted.

It is advantageous that during discharge of the at least one component, a complete overlap or engaging of the corresponding bayonet projections allows a high power transmission and the applicator is, therefore, securely fixed to the container even at high discharge pressure.

In a further embodiment of the invention, the bayonet projections of the receptacle of the container and/or the connection portion of the applicator are at least partially formed with bevels allowing the applicator closing on the container when turning the applicator into the storage position and/or the delivery position. This achieves a particularly good sealing between the applicator and the container.

It is further preferred if the container has a flange-like holding section with an enlarged outer diameter on its (proximal) end opposite of the receptacle for the applicator. This holding portion may serve for attachment within a dispensing gun or for use of the container as a syringe.

According to a preferred embodiment of the invention catch means are provided on the container and/or the applicator, which allow a relative rotational movement of the applicator to the container in a first rotational direction and prevent rotational movement in another, in particular opposite, direction of rotation.

In other words, the catch means do not or only slightly influence the rotational movement in the first direction of rotation, while the rotational movement in the other direction is hindered such that this rotation is manually, i.e. without auxiliary means, not possible by the user. Particularly preferably, a rotational movement in the other direction is not possible without damaging or destroying the container and/or applicator.

It is particularly preferred if the catch means hinder a relative rotational movement between the applicator and the container. Thereby it is advantageous that an unintentional rotation of the applicator is prevented or at least made more difficult in the provision position. In particular, the catch means can define a certain direction of rotation, for example, from the mounting into the storage position and/or from the storage in the provision position, are given by increased rotational resistance.

These functions can be achieved, for example, in that the catch means form a projection on the applicator, which engage in catch means, e.g. catch recesses, provided on the container, if the applicator is connected to the container, i.e. in the assembly, storage and/or provision position. To impede a relative rotation between applicator and container, the shape of the catch means can be adjusted. In this case, it is preferable to form the catch means as essentially semicircular recesses on the container. If the applicator is rotated, the catch means fixed thereto must be rotated out of the recess. For this purpose, a rotation over a corner of the recess and a corresponding force is necessary. If the rotation of the applicator should be impeded in one direction of rotation only, the substantially rectangular corners of the semicircular recesses may be little or not at all rounded. The less the corners of the semicircular recesses are rounded, the harder is a rotation of the catch means of the applicator over the corresponding corner. Accordingly, a direction of rotation can be preferred by a significant rounding of the corners of the catch means, so that less force is required for rotation in this direction and the rotation is made easier in this direction.

In a preferred embodiment of the invention, the first blocking element provided on the plug is a web or a protrusion and the second blocking element provided on the applicator is a web or a protrusion which overlaps with the web or protrusion of the plug at least in the storage position. In this case, the protrusion of the first blocking element on the plug may have distal contact surfaces (facing the applicator) and the second blocking element (on the applicator) may have proximal contact surfaces, wherein the distal and proximal contact surfaces facing each other and contact each other in the storage position.

Particularly preferred are cross-shaped webs as the first blocking element. The second blocking elements are preferably formed as approximately quarter-circle-shaped blocks within the connecting portion of the applicator. The at least two, preferably four, blocks are arranged equidistantly on a circular path and between the blocks recesses are provided, which can receive the first blocking elements, for example the webs, in the provision position of the applicator. This may also be slots corresponding to the first locking elements, so that a displacement of the plug is only possible with an exact positioning of the applicator in the provision position. An advantage of the above-described embodiment is the particularly stable fixing of the plug in the storage and discharge position.

As an alternative to the preferred embodiment of the invention described above, the blocking elements can also be designed as a lateral projection or groove. Thus, the first blocking element can be formed as a lateral bayonet projection on the plug. In this embodiment of the invention, the second blocking element is formed as one partially circumferential and partially axially extending bayonet groove for receiving the bayonet projection of the plug in the provision position of the applicator and is formed in the interior of the connection section of the applicator. Thus, the plug can be moved only in an exact positioning of the applicator in its provision position.

In a further embodiment of the invention, the first and second locking elements are designed such that the plug is not displaceable relative to the applicator in the mounting position of the applicator. In this case the applicator can press the plug into the chambers while mounting the applicator on the container, so that any incorrect or incomplete assembly of the plug into the container would be automatically corrected by attaching the applicator.

It is further preferred, if the plug has at least one (inner or outer) bypass channel through which a flow connection is established from chamber to applicator in its dispensing position. In this case a, for example annular, axially continuous recess can be provided in the plug, which is interrupted with webs for fixed connection of the portions separated by the recess. If, for example, two such webs are provided, four openings are formed within the recess through which the at least one component can flow in the direction of the applicator and be applied.

For this purpose, it is appropriate if the at least one chamber has at least one outlet opening, and in that the plug has at least one closure section, which, in the storage position of the plug, is inserted into the outlet opening in a closing manner. If a plurality of chambers are provided, these each have at least one outlet opening into which a closure section of the plug is inserted in a sealing manner. Compared to a substantially flat plug, which merely covers the outlet openings, an increased tightness is achieved by such a design of the plug. In particular, unintentional mixing of the components becomes virtually impossible in the closed state of the container, since the components would not only have to displace the plug, but would also have to flow around a plurality of corners (so-called closure edges) formed by the closure sections.

According to a particularly preferred embodiment of the invention, the plug is guided in the container in the storage position and possibly also in the discharge position to prevent rotation, tilting and jamming. As a result, it is prevented that the plug is twisted without transferring the applicator to its provision position so that the plug takes a position relative to the applicator that would allow the plug to be displaced in the storage position. This can be achieved by appropriate coding means on the plug, which engage in recesses provided within the housing of the container, which allow both a torque-proof guiding in the storage position and, with a corresponding length of the coding means, in the discharging position of the plug. In the discharging position, it is also possible to prevent twisting of the plug by appropriate design of the first and second blocking elements, for example, by guiding the first blocking elements in corresponding recesses between the second blocking elements.

For example, the plug may have a substantially circular disk-shaped basic form and sealing means on its (proximal) side facing the at least one chamber and/or on its outer circumference. On its (distal) side facing away from the at least one chamber, a blocking element formed by two webs extending at right angles to one another can be provided. Furthermore, the plug preferably has at least one breakthrough as a bypass channel.

The at least one chamber is closed on its side facing away from the plug (proximal) side with a piston. The piston is axially displaceable in the respective chamber. According to a particularly preferred embodiment, the piston is connected via at least one defined breaking point in one piece with the container. This facilitates the mounting of the container. The piston may e.g. be separated before or during filling of the container from the same to be freely displaced in the chamber.

In addition, the container may be formed with a separate plunger, which is suitable for insertion into the at least one chamber and for displacing the piston. For containers with two concentrically arranged chambers, a distal portion of the plunger is configured with an outer cylinder for the outer piston and a central pin for the inner piston. It may be advantageous, if the pin protrudes or is put back from the cylinder such that e.g. forerun caused by different viscosities of one of the components during discharge is prevented or at least to reduced.

The container may also be formed like a syringe with a support surface for fingers and a corresponding counter bearing on the plunger. This allows to discharge components without a dispensing gun manually from the container.

In addition to the advantage that unintentional opening of the plug is prevented by a rotation in the storage position relative to the applicator, the plug is also guided during displacement into the dispensing position, such that tilting or jamming of the same is prevented in the container, which otherwise causes problems during discharging of the at least one component, e.g. by blocking the flow connection between the container and applicator or by only releasing only one discharge channel, so that the mixing ratio of two components is disturbed.

The problem underlying the invention is also solved by a method for discharging at least one component from a container, for example a container as described above. For this purpose, the container has at least one chamber, which is closed by a plug on a first side, and with an applicator rotatably mounted on the first side, which prevents axial movement of the plug in a storage position. The method comprises the following steps: rotating the applicator relative to the container into a provision position, in which the applicator does not prevent an axial movement of the plug, and then displacing the plug, preferably by the internal pressure of the at least one component, from a storage position, in which a flow connection between the chamber and the applicator is blocked by the plug, into a discharge position, in which the chamber is in fluid communication with the applicator.

According to a preferred embodiment of the method, rotation of the applicator is permitted by catch means provided on the container and/or the applicator in a first direction of rotation and is prevented in another direction of rotation. In other words, turning in the first direction of rotation is little or not affected by the catch means, while turning in the other, in particular opposite, direction of rotation is difficult to the extent that it can no longer be done manually by the user, i.e. without auxiliary means.

Particularly preferred, turning in the other direction of rotation is not possible without damaging or destroying the container and/or applicator.

Before discharging the at least one component, the container is assembled and filled with the at least one component. For this purpose, the piston is inserted at first into the at least one chamber and guided to the distal end of the chamber. Via this end, the chamber can then be filled with displacement of the piston in the proximal direction. Subsequently, the plug is placed for sealing onto the at least one chamber. Finally, the applicator is mounted in the mounting position on the container and in particular already factory-rotated by the manufacturer into the storage position. The container is thus sealed tight and the components can be safely stored. Preferably, the container is stored and shipped in the storage position. The user of the container, which must discharge the components, can transfer the applicator in its provision position by relative rotation to the container. In this position, the container is not yet open. Rather, in particular by the internal pressure of the components, a flow connection between the chambers and the applicator is made after displacement of the plug, so that components can be discharged.

Thus, in a preferred embodiment, a container according to the invention has an assembly, storage, and provision position for the applicator, and a storage and discharging position for the plug, wherein the discharging position of the plug and the delivery position of the applicator are different are decoupled so that the plug in the provision position of the applicator initially seals the at least one chamber in its storage position.

The invention is explained in more detail by means of embodiments and with reference to the drawings. All described and/or illustrated features, alone or in any combination, form the subject matter of the invention independently of their summary in the claims or their relationships.

Shown schematically

Figure 2:
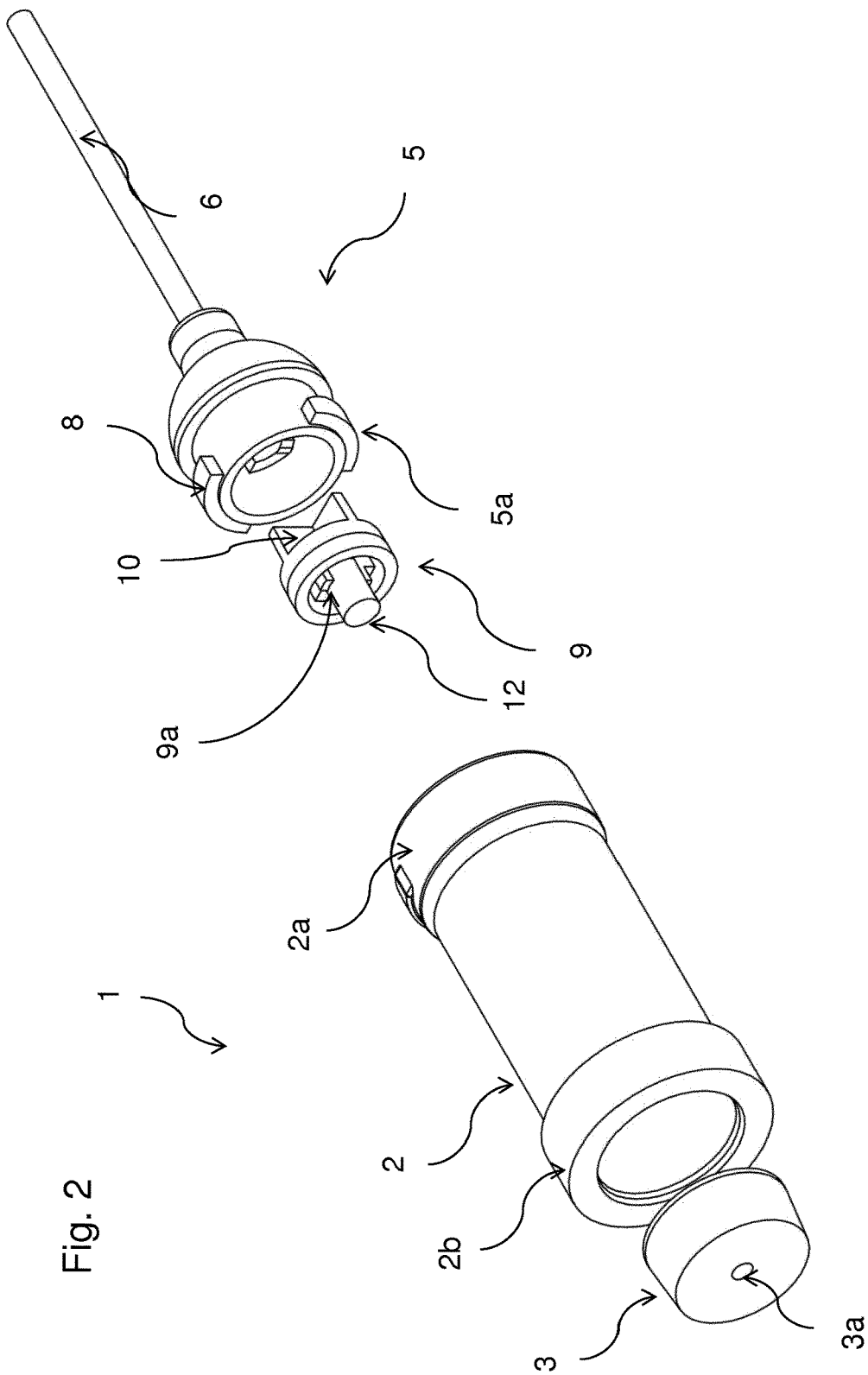
Figure 4D:
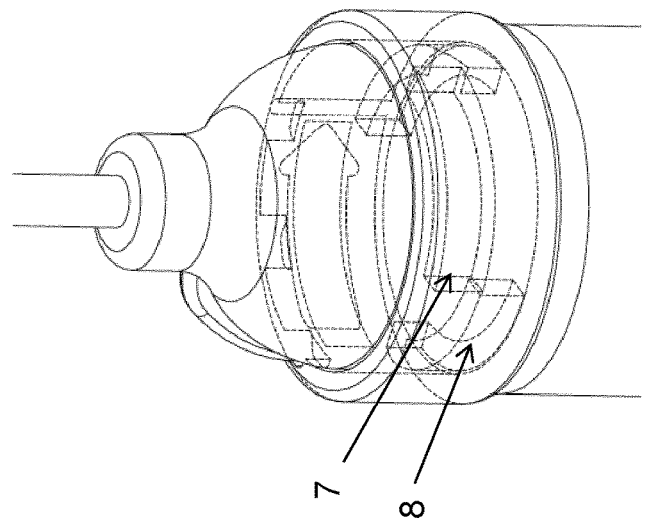
Figure 4C:
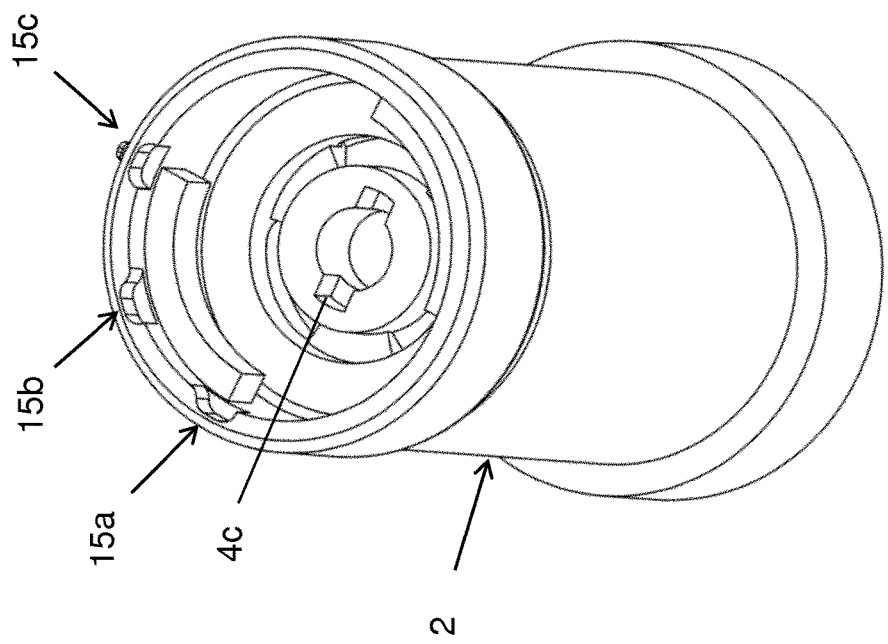
Figures 5A, 5B:
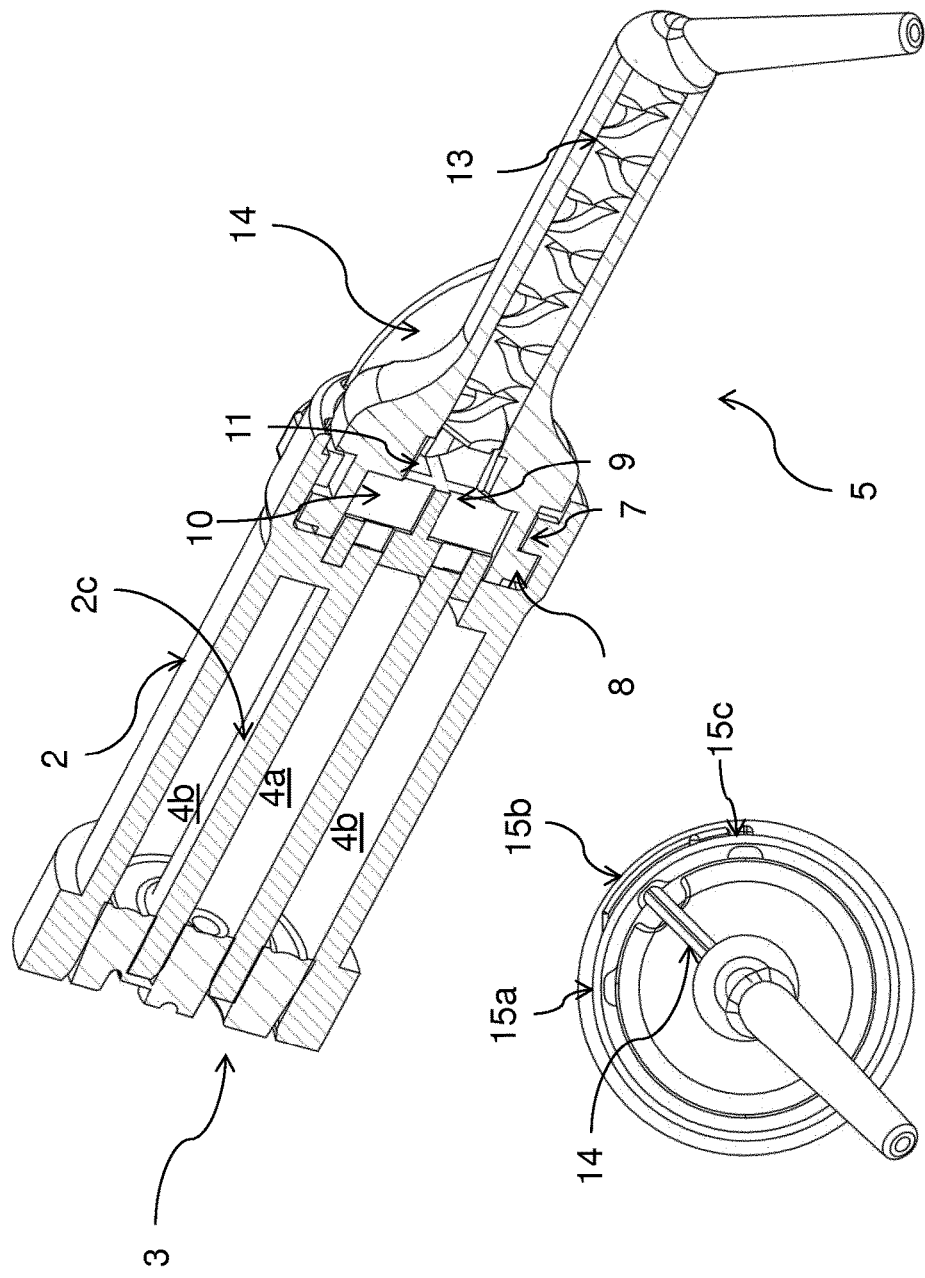
Figures 6A, 6B:
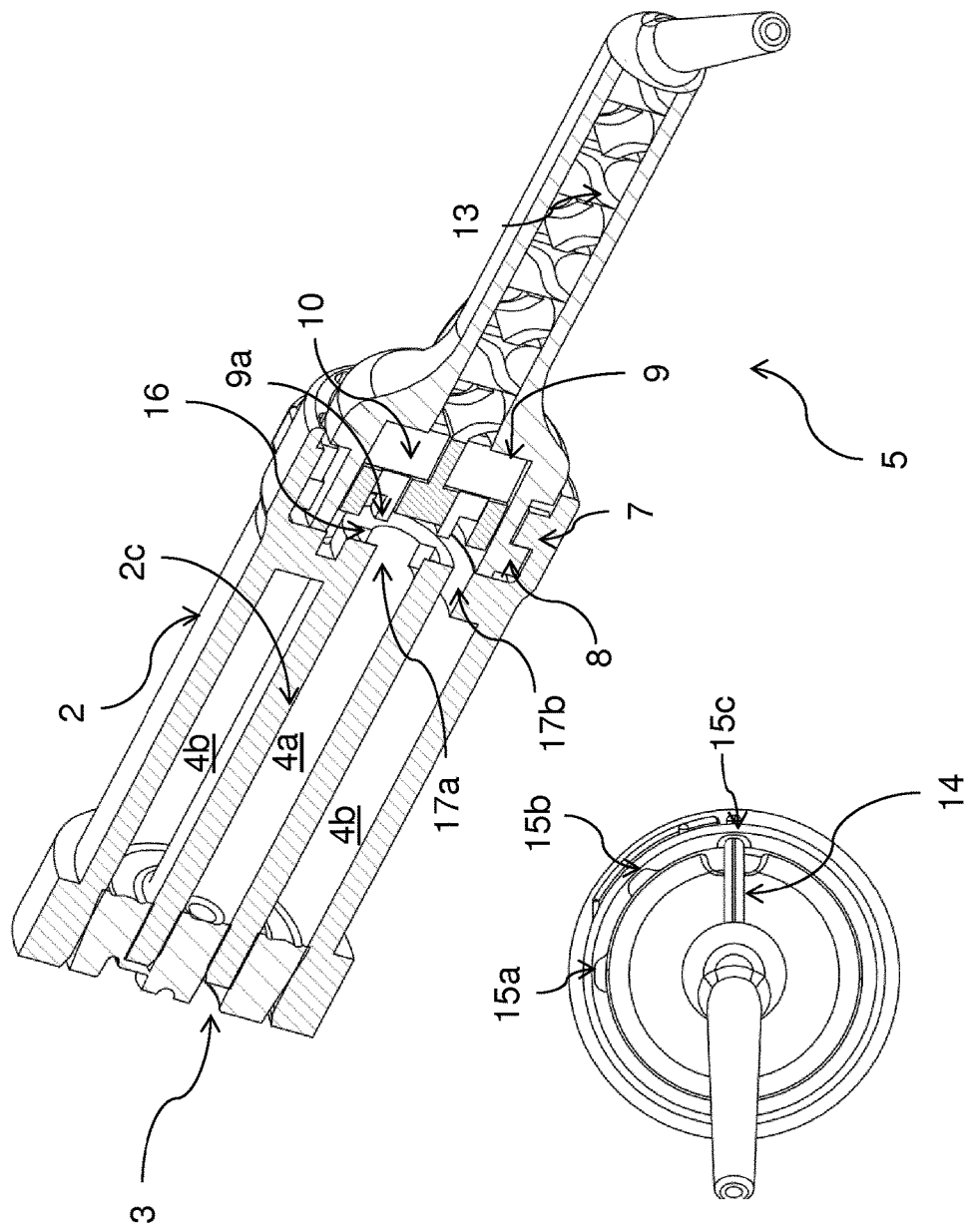
Figure 7:
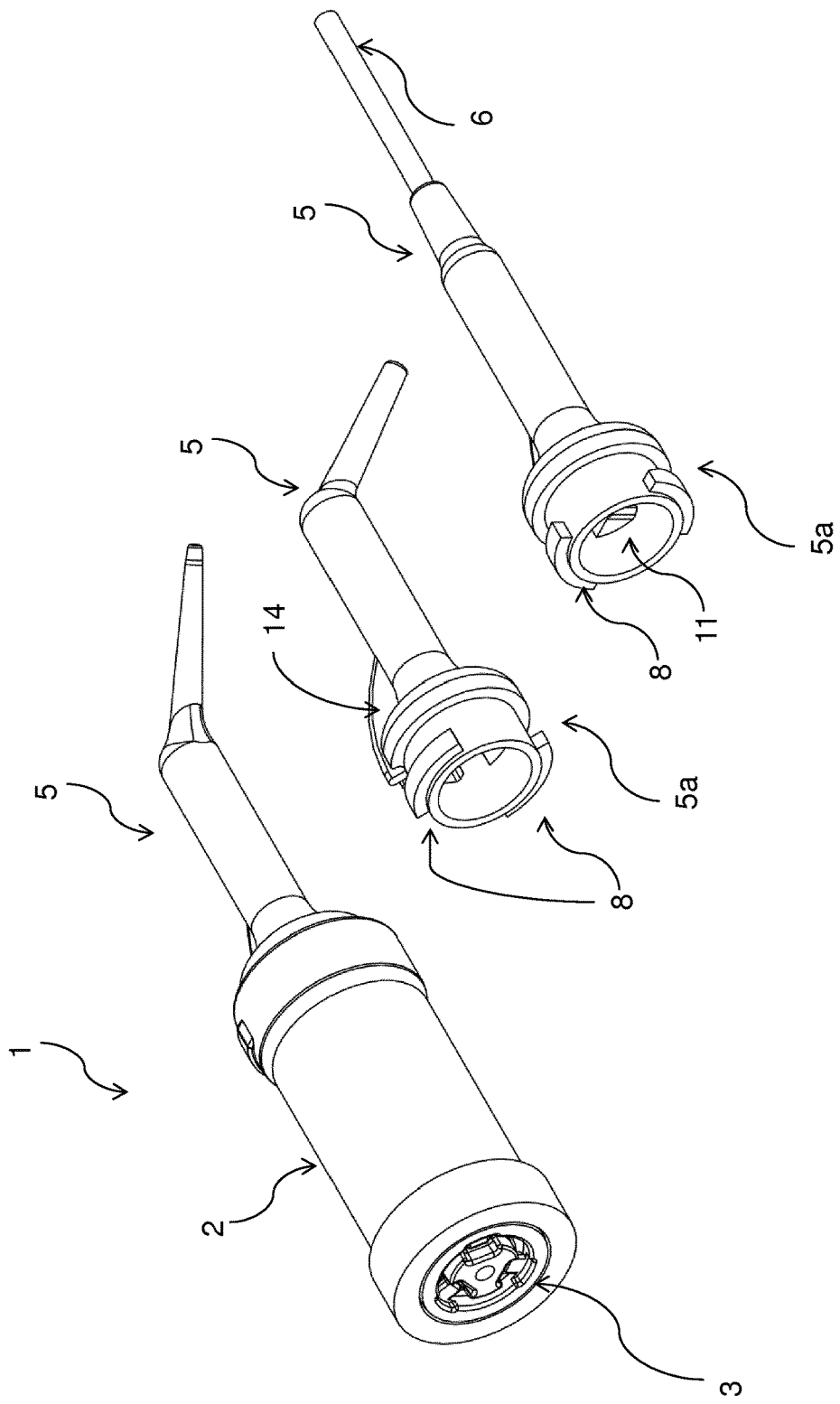
Figure 8C:
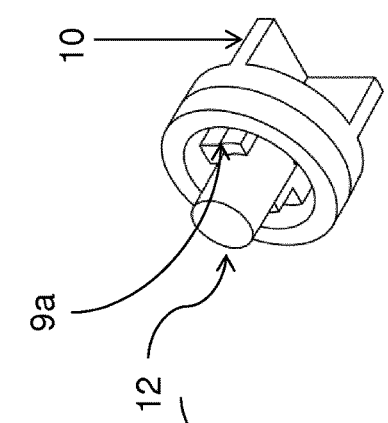
Figure 8B:
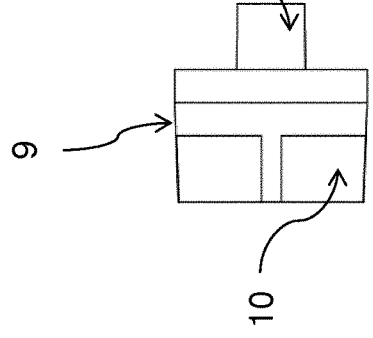
Figure 8A:
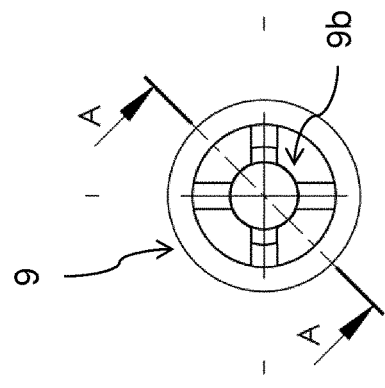
Figure 9C:
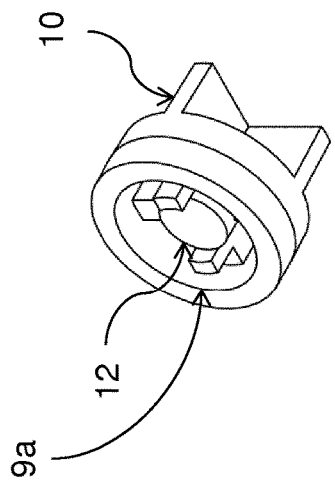
Figure 9B:
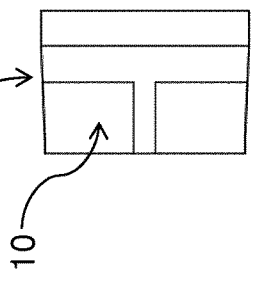
Figure 9A:
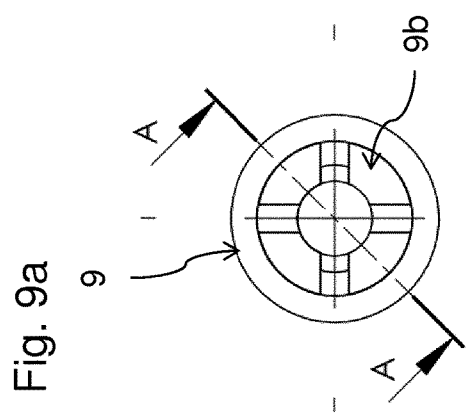
Figure 12:
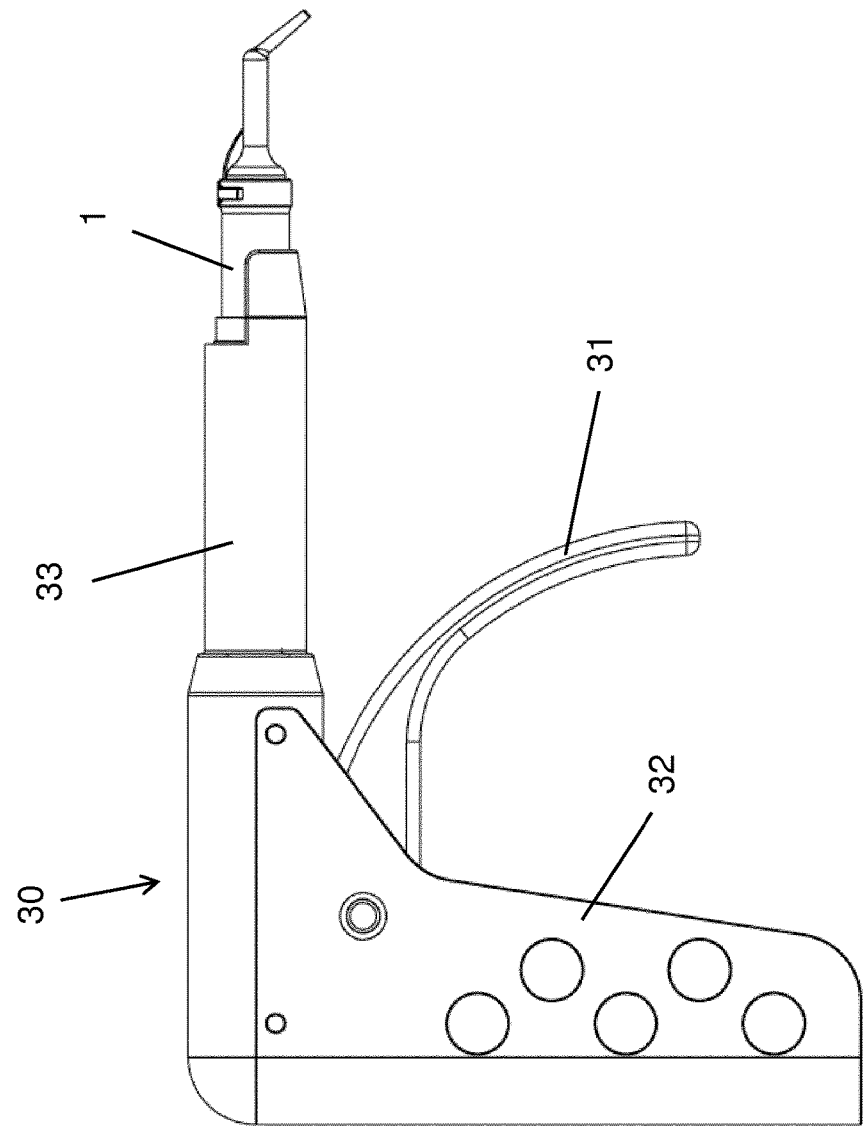
Figure 13A:
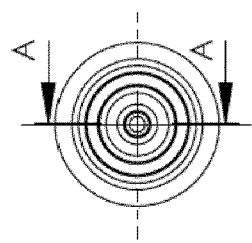
Figure 14A:
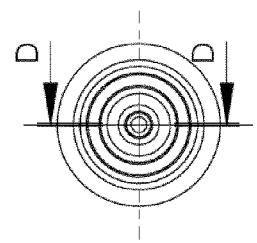
Figure 13B:
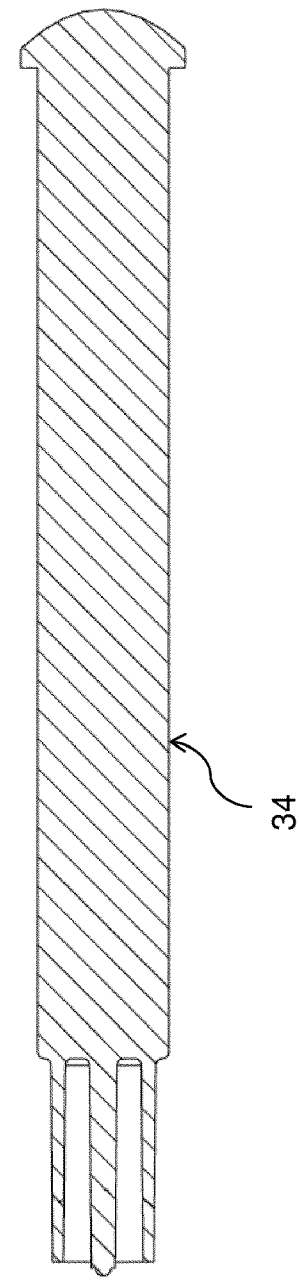
Figure 14B:
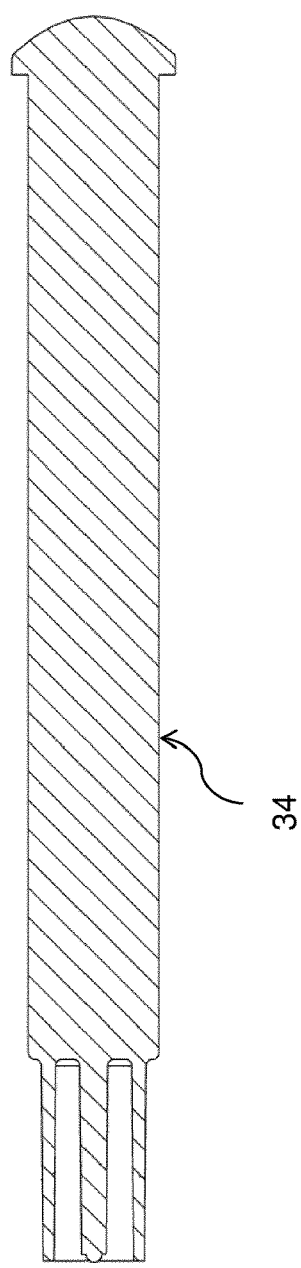
Figure 16A:
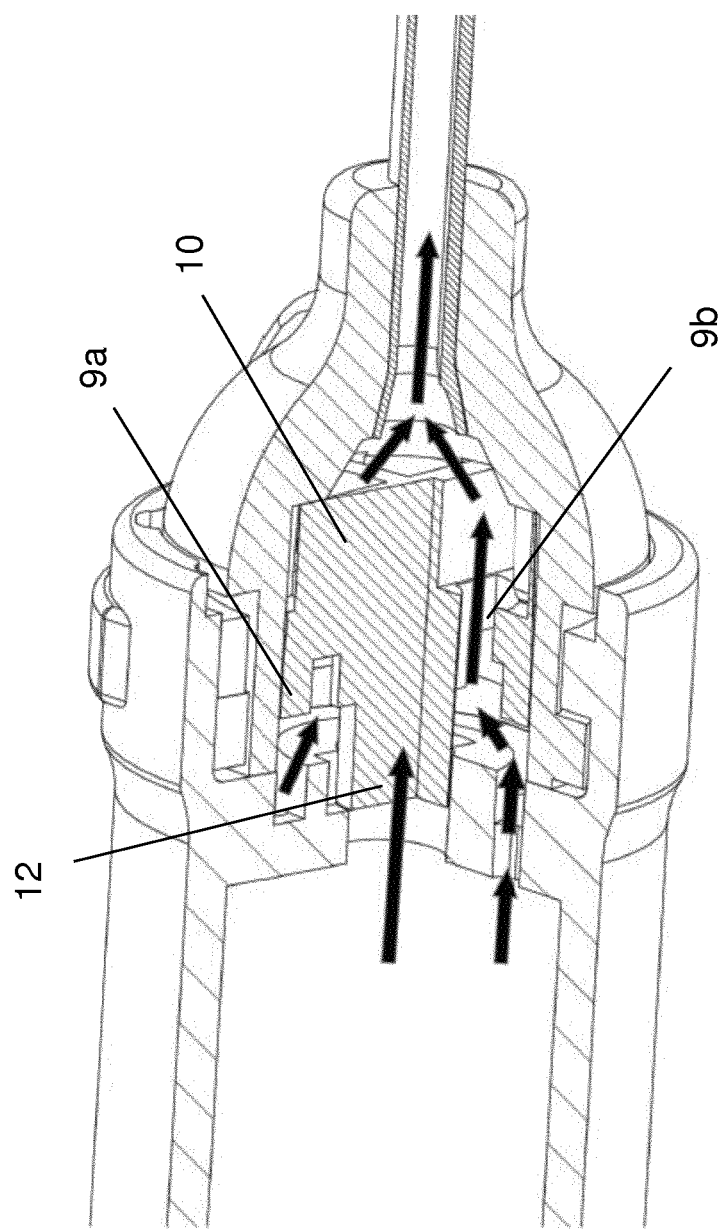

FIG. 1 a longitudinal section of a container according to the invention according to a first embodiment, FIG. 2 an exploded view of the components of the container shown in FIG. 1, FIG. 3 an exploded view of the components of a container according to the invention according to a second embodiment, FIG. 4*a* a longitudinal section of the container shown in FIG. 3 in the mounting position of the applicator, FIG. 4*b* a top view of the container shown in FIG. 4*a*, FIG. 4*c* a top view of the container shown in FIG. 4*a* without applicator, FIG. 4*d* a partially broken view of a detail of the container shown in FIG. 4*a*, FIG. 5*a* a sectional view of the container shown in FIG. 3 in the storage position of the applicator, FIG. 5*b* a top view of the container shown in FIG. 5*a*, FIG. 5*c* a partially broken view of a detail of the container shown in FIG. 5*a*, FIG. 6a a sectional view of the container shown in FIG. 3 in the provision position of the applicator and the discharging position of the plug, FIG. 6b a top view of the container shown in FIG. 6a, FIG. 6c a partially broken view of a detail of the container shown in FIG. 6a, FIG. 7 the container of the second embodiment and two further applicators according to the invention, FIG. 8a-c the plug shown in FIG. 2 in top view, in longitudinal section and in perspective view, FIG. 9a-c the plug shown in FIG. 3 in top view, in longitudinal section and in perspective view, FIG. 10a-c the piston shown in FIG. 2 in perspective view, in top view and in longitudinal section, FIG. 11a-c the piston shown in FIG. 3 in perspective view, in top view and in longitudinal section, FIG. 12 a side view of a gun for use with a container shown in FIG. 1 or 3, FIG. 13a-b a plunger of the gun shown in FIG. 12 in top view and in longitudinal section, FIG. 14a-b a alternative plunger of a gun shown in FIG. 12 in top view and in longitudinal section, FIG. 15a-c a further embodiment of a container according to the invention in perspective view, exploded view and longitudinal section, and FIG. 16a-b a partially broken view of the flow pattern of the components in the open state of the container shown in FIG. 1 or FIG. 3, respectively.

In FIGS. 1 and 2, a container 1 according to the invention is shown. The container 1 is formed with housing 2 substantially cylindrical on the in- and outside and is sealed at the proximal end by a piston 3. In this embodiment only one chamber 4 is formed for receiving a component within the housing 2. The piston 3 can be moved, for example by means of a gun 30 shown in FIG. 12, in the direction of the first (distal) side, i.e. to the right in FIG. 1, whereby the volume of the chamber 4 is reduced specifically. To improve the mechanical connection of a plunger of a dispensing gun with the piston 3, the same preferably exhibits a notch 3a, which can partially receive the tip of the plunger of the dispensing gun and thus prevents or at least impedes slipping of the plunger.

Attached to the container 1 is applicator 5, in the embodiment of FIG. 1 provided with a cannula 6. For this purpose, the container 1 has a sleeve-like receptacle 2a with radially inwardly directed bayonet projections 7 for attaching an applicator 5 on the first (distal) side facing the applicator 5. The applicator 5 has a socket-like connection section 5a with radially outwardly directed bayonet projections 8. The bayonet projections 7 and 8 allow the applicator 5 to be mounted in a mounting position on the container 1 and to transfer the applicator 5 by rotating into a storage position and into a provision position.

In the area enclosed by the socket-like connection section 5a of the applicator 5, a plug 9 sealing chamber 4 is provided between the applicator and the container 1. In the storage position of the plug 9 shown in FIG. 1, the same is held non-displaceable in the container 1. This is achieved by means of a first blocking element 10 formed on the plug 9 and a second blocking element 11 formed onto the applicator 5, which in this position are aligned with one another such that they prevent displacement of the plug 9 relative to the applicator and thus also relative to the container 1. In this preferred embodiment, the plug 9 has coding means 9a which prevent rotation of the plug 9 relative to the chamber 4. For this purpose, the chamber 4 has corresponding coding means 4c. Thereby, a correct positioning of the plug 9 is ensured and inadvertent rotation of the first and second blocking elements 10 and 11 to each other due to rotation of the plug 9 is prevented.

In the state of the container 1 shown in FIG. 1, the applicator 5 is already pre-installed on the container 1 in such a way that the container can be put into use without further assembly steps. It is particularly advantageous that the current embodiment of the invention allows pre-mounting and usage of a metal cannula 6 by the manufacturer, which shows no visible corrosion during storage of corrosive and/or caustic substances in the chamber 4 during prolonged storage (e.g. more than 2 weeks).

The housing 2 of the container 1 is preferably provided with a retaining section 2b on the (proximal) side facing away from the applicator 5, wherein retaining section 2b projects radially from the container 1. In this case, the retaining section 2b has a flange-type outer diameter being larger than housing 2, so that the container can be held securely against displacement in a dispensing gun. The retaining section 2b is thus suitable for fastening the container in a dispensing gun according to U.S. Pat. No. 8,602,775 B2. A gun 30 for receiving and actuating the container is shown in FIG. 12. The gun has an actuation handle 31, a holding section 32 and a receiving channel 33 for insertion of the proximal end of a container 1. A plunger, not shown in FIG. 12, may displace the piston 3 of the container 1 to discharge the component from the chamber 4.

The first blocking elements 10 of the plug 9 are also shown in FIG. 2. The blocking elements 10 form a cross arranged on the side of the plug 9 facing the applicator 5, wherein the blocking elements 10 are formed preferably radially continuous, that is to say from one radial end of the plug 9 to the opposite radial end. For the embodiment of FIGS. 1 and 2 with a single chamber 4, the plug 9 is preferably formed with a proximally protruding closure portion 12. By this closure portion 12, the chamber is sealed particularly secure, so that even at elevated thermal stress (e.g., temperatures above 30° C.) and/or mechanical shocks of the container pouring of the component stored in container 4 past plug 9 can be prevented by the same.

FIGS. 3 to 6 show a further embodiment of a container 1 according to the invention having two chambers 4a and 4b, which, in this example, are concentric with one another and separated from each other by a partition wall 2c. The volume of the chambers 4a and 4b depend on the desired ratio, for example. 10:1 to 1:1, in particular 1:1, 1.5:1, 2:1, 4:1, 5:1 and 10:1, and may be adapted to the components stored in the chambers. In this embodiment, the applicator 5 comprises a mixing helix 13, which can be freely rotatable mounted in the applicator 5. Alternatively, the mixing helix 13 is integrally connected to the plug 9.

FIGS. 4 to 6 show in sectional view and top view different positions of the applicator 5 and their effect on securing the plug 9 of a container 1 according to FIG. 3.

FIG. 4 a shows a sectional view of a container 1 in the assembly position according to FIG. 3, wherein the applicator 5 is detachably connected to the housing 2. Furthermore, a catch means 14 is shown in the depicted position, which forms an attack surface for manual rotation of the applicator 5. Therefore, the radially inwardly directed bayonet protrusions 7 of the container 1 and the radially outwardly directed bayonet protrusions 8 of the applicator 5 slide past one another in the axial direction, namely they do not overlap one another. In this position, the applicator 5 can therefore be separated non-destructively from housing 2.

FIG. 4b shows catch means of the container 1 provided on the side of the housing 2 facing the applicator and formed semicircular recesses 15a, 15b and 15c. Therein a catch means 14 provided on the connection section 5a of the applicator 5 engages (FIGS. 5b and 6b). The recesses 15a-c allow a precise and defined rotational position of the applicator 5 in mounting (FIG. 4), storage (FIG. 6), and provision position (FIG. 6), and impede rotation of the applicator 5 to prevent inadvertent rotation. FIGS. 4d, 5c and 6c show the position of the radially inwardly directed bayonet protrusions 7 of the container 1 and the radially outwardly directed bayonet protrusions 8 of the applicator 5 in the three rotational positions, i.e. in the mounting position, in the storage position and in the provision position.

The shape of the catch means 15a-c formed on the container 1 (see FIG. 4c) is such that rotation from the mounting position to the storage position takes place via a rounded corner of the semicircular recess 15a. Likewise, the rotation from the storage position to the provision position via considerable rounded corners, so that little force must be applied for rotation of the applicator in this direction of rotation.

FIG. 5a again shows, in a sectional view, a container 1 according to FIG. 3 in the storage position of the applicator 5. In the storage position, the first and second blocking elements 10 and 11 are aligned with one another such that a displacement of the plug 9 in the distal direction is prevented. In addition, in the storage position, the bayonet projections 7 and 8 overlap at least partially with each other (FIG. 5c), so that a non-destructive removal of the applicator 5 from the housing 2 is not possible in this position. FIG. 5b shows the top view of the container 1 in the storage position of FIG. 5a.

FIG. 6a shows a sectional view of a container 1 according to the invention according to the embodiment of FIG. 3 in the discharging position. In addition, to illustrate the operation of the flow connection between the chambers 4a/4b and the applicator 5, the plug 9 is shown displaced from its storage position to its discharging position, while piston 3 is still shown in its initial position. After the forward movement of the plug 9 in the axial direction, the first and second blocking elements 10 and 11 in the axial direction at approximately the same height but laterally offset from one another.

In the provision position of FIGS. 6a and 6b, the bayonet protrusions 7 and 8 overlap in such a way that the applicator is firmly held on the housing 2 even at high application pressure. Preferably, the form closure of the bayonet protrusions 7 and 8 in the provision position is at a maximum, i.e. the bayonet protrusions 7 and 8 overlap on the entire length of at least one of the bayonet projections.

In FIG. 6a, the coding means 9a of the plug 9 are shown. If the plug 9 seals the chambers, as shown in FIGS. 4a and 5a, these coding means 9a engage in recesses 16 provided here on the partition wall 2c, whereby only a certain orientation of the plug 9 for closing the chambers 4a, 4b is possible, otherwise the coding means 9a prevent a fitting placement of the plug 9. In addition, when displacing the plug 9, the same is guided in the recesses 16, as long as the coding means 9a still engage with the recesses 16. This prevents tilting, jamming or twisting of the plug 9 when displaced into the discharging position, which has often led to problems during discharging the components in conventional containers.

By moving the plug 9 in its discharging position, discharge openings 17a and 17b of the chambers 4a and 4b are unblocked. Therefore, the components can initially flow through the discharge openings 17a and 17b into the space between the housing and plug. This may already lead to a certain pre-mixing of the components, which subsequently continue to flow through the plug 9 and past the blocking elements 10 and 11 into applicator 5, in which they are further mixed by the mixing helix 13.

FIG. 7 shows a container 1 according to the second embodiment with applicator 5 and two further examples of suitable applicators. Also shown are catch means 14 provided on the applicator 5, the radially outwardly directed bayonet protrusions 8 and second blocking elements 11 arranged in the interior of the receiving portion 5a of the applicator 5.

FIG. 8 depicts the plug 9 according to the first embodiment with fastening section 12, coding means 9a and blocking element 10. In the plan view of plug 9, also shown in FIG. 8, the preferably cross-shaped configuration of the blocking element 10 is illustrated. In addition, recesses 9b formed by the free space between the webs of the blocking element 10 are shown, which form a bypass channel in the discharging position of the plug.

FIG. 9 shows a plug 9 for a container with two concentric chambers. In this case, the closure section 12 is made shorter to allow a higher volume of the internal chambers.

In FIG. 10a-c, piston 3 according to the first embodiment is shown having notch 3a in a perspective drawing (FIG. 10a), as a plan view (FIG. 10b) and side view (FIG. 10c). The piston 3 has a seal 18 on the (distal) side facing the applicator 5 in order to seal the chamber airtight. It is also advantageous that when discharging the components almost no residues remain within the chamber.

In FIGS. 13a, 13b, 14a and 14b, the piston rods or plungers 34 and 34 corresponding to the notch 3a are shown. These are designed with coaxial discharge contours such that an inner discharge protrudes over an outer discharge contour being located opposite to the inner discharge contour (FIG. 13a, 13b) or vice versa (FIG. 14a, 14b).

In this way, a potential forerun of a base or catalyst component in one of the chambers of the container can be compensated. These plungers can also be used for containers with only one chamber, in which case the variant according to FIGS. 14a and 14b is preferred, since the application force can be better transmitted to the piston through the outer annular contact surface of the plunger.

In addition, this discharge contour can also be used for a 1-component compule. Particularly preferred here is the outer discharge contour on the inner discharge contour out to evenly distribute the forces over a larger area here.

In FIG. 11a-c, the piston 3 is shown for a container with two concentric formed chambers. In the perspective drawing shown in FIG. 11a, an annular, axially almost continuous recess 19 is shown, which receives the partition 2c when the piston is pressed into the housing 2 with the chambers 4a, 4b. The piston 3 comprises sections 3b (cylindrical) and 3c (annular) corresponding to the two chambers 4a, 4b, which are arranged with seals 18 at the transition of a chamber to a wall limiting the chamber, for example the partition wall 2c. Although the radially inner portion 3b and the radially outer portion 3c are guided separately in the chambers, the piston 3 of a preferred embodiment is integrally formed, which greatly simplifies the assembly of the container and the filling with the components. For this purpose, preferably three, webs 20 are preferably provided between the sections 3b and 3c and are broken off during insertion of the piston 3 into the container through the partitions wall 2c, so that the sections 3b and 3c can be guided separately in the chambers 4a and 4b. In other words, the integrally designed piston 3 automatically divides during assembly into two sections 3b and 3c separately guided into the chambers.

It is preferred if the webs 20 are fixed to the radially inner portion 3b with a rupture edge, which is designed to be significantly thinner compared to the thickness of the webs 20 and thereby forms a predetermined breaking point. Further, it is preferable to form the webs 20 on the radially outer portion 3c so as to prevent the webs 20 from breaking off at the portion 3c. In other words, the webs 20 break off only at the radially inner portion 3b and remain connected to the radially outer portion 3c. This can prevent the webs 20 from being completely separated from the sections 3b and 3c and blocking the piston 3 from being pushed into the housing 2.

In a further preferred embodiment, the radially outer portion 3c has a recess 21 which can receive the webs 20 broken from the radially inner portion 3b. In other words, when inserting the piston 3 into the housing 2, the webs 20 fold away into the recesses 21 of the radially outer section 3c provided for this purpose, and then lie substantially flush at the side of the section 3c facing the partition wall 2c. The recesses 21 therefore allow a reception of the webs 20, whereby blocking of the sections 3b and 3c is prevented. A further effect of the recesses 21 can be seen in the fact that damage to the partition wall 2c is prevented by the webs 20 broken off at the section 3b, whereby a leakage of a chamber due to damage to the walls and greatly reduced storage stability is prevented.

A further embodiment of the invention is shown in FIGS. 15a to 15c. The container 1 is designed as a syringe, which can be operated manually without a pistol (FIG. 12). For this purpose, the retaining section 2b compared to the embodiments according to FIG. 1 or 3 is formed enlarged as a flange, which serves to support fingers during actuation.

In addition, a plunger 34 is provided, which comprises an enlarged support surface for manual operation at its proximal end. In the illustrated embodiment, the container is configured with two mutually coaxial chambers and with a plunger 34 having a pin-like inner portion and a cylindrical outer portion, i.e. for two components. Accordingly, the piston 3 has two separate piston elements. However, it is also possible to provide the syringe-like configuration for containers with only one chamber or with multiple chambers.

The flow path of the components in the open state of the container from the respective chamber into the applicator is shown in FIGS. 16a and 16b for a one-component container and a two-component container. It can be seen how the components shown by arrows in FIGS. 16a and 16b apply pressure on the respective plug 9 in order to displace it in the direction of the applicator 5 until the components can pass through the respective bypass channel 9b through the plug 9 or can pass the plug 9 entirely.

REFERENCE SIGNS

| | |
|---|---|
| 1 | container |
| 2 | housing |
| 2a | receptacle |
| 2b | retaining portion |
| 2c | partition wall |
| 3 | piston |
| 3a | notch |
| 3b | cylindrical section |
| 3c | annular section |
| 4 | chamber |
| 4a, 4b | chamber |
| 4c | coding means |
| 5 | applicator |
| 5a | connection section |
| 6 | metal cannula |
| 7 | bayonet protrusion |
| 8 | bayonet protrusion |
| 9 | plug |
| 9a | coding means |
| 9b | bypass channel |
| 10 | blocking element |
| 11 | blocking element |
| 12 | closure section |
| 13 | mixing helix |
| 14 | locking means |
| 15a-15c | recess |
| 16 | recess |
| 17a, 17b | discharge opening |
| 18 | sealing |
| 19 | recess |
| 20 | web |
| 21 | recess |
| 30 | gun |
| 31 | actuation handle |
| 32 | retaining section |
| 33 | receiving channel |
| 34 | plunger |

The invention claimed is:

1. A container for storing and discharging a component, the container having a chamber sealed on a first side by a plug and an applicator mounted on the first side, wherein the plug is displaceable relative to the chamber from a storage position, in which a flow connection between the chamber and the applicator is interrupted by the plug, to a discharging position, in which the chamber is in flow communication with the applicator, characterized in that a flow connection between the chamber and the side of the applicator facing away from the chamber is configured to be opened by a rotation of the applicator relative to the container and a subsequent axial movement of the plug relative to the container and the applicator, due to pressure exerted on the plug by the component and in that the plug has a first blocking element and the applicator has a second blocking element, and that the applicator is rotatable relative to the chamber from a storage position, in which the blocking elements are aligned with each other, so that the blocking elements prevent a displacement of the plug, to a provision position, in which the blocking elements are aligned with each other so that axial displacement of the plug, by the internal pressure of the component, is enabled, wherein the plug has a substantially circular disk-shaped form and periphery sealing means located on a side of the plug facing the chamber and/or on an outer circumference of the plug, and a blocking element formed by mutually perpendicular webs and located on the side of the plug facing away from the chamber and a breakthrough as a bypass channel, and wherein the plug further has coding means which prevent rotation of the plug relative to the chamber, the chamber having corresponding coding means in the form of recesses provided within the housing of the container.

2. The container according to claim 1, characterized in that locking means are provided on the container and/or the applicator, the locking means allowing a rotational movement of the applicator relative to the container in a first rotational direction and preventing rotation in an opposite rotational direction.

3. The container according to claim 1, characterized in that the applicator is axially fixed to the container in the storage position and in the provision position.

4. The container according to claim 1, characterized in that the applicator is rotatable from a mounting position, in which the applicator can be attached axially on the container, relative to the chamber first into the storage position and then further into the provision position.

5. The container according to claim 1, characterized in that the container has a receptacle for the applicator with a radially inwardly directed bayonet protrusion and the applicator has a connection portion, which is insertable in the receptacle, with a radially outwardly bayonet protrusion and has a flange-like retaining portion with enlarged outer diameter on its the receiving opposing end of the container.

6. The container according to claim 2, characterized in that the locking means impede a relative rotational movement between the applicator and the container.

7. The container according to claim 3, characterized in that the first blocking element is a web or a projection on the applicator, and that the second blocking element is a web or a projection, which at least in the storage position overlaps with the web or projection of the plug.

8. The container according to claim 1, characterized in that the plug has at least one bypass channel through which a flow connection from the chamber to the applicator is established in a discharge position of the plug.

9. The container according to claim 2, characterized in that the chamber has a discharge opening, and that the plug has a closure section, which in the storage position of the plug is inserted sealingly into the discharge opening.

10. The container according to any claim 2, characterized in that the plug has an outer contour and is non-rotatably guided in the container both in the storage position and in the discharging position.

11. The container according to claim 1, characterized in that the chamber is sealed with a piston on a side of the chamber facing away from the plug, which is integrally formed with the container via a predetermined breaking point.

12. The container according to claim 1 with a separate plunger, which is configured for insertion into the chamber.

13. The container according to claim 10, wherein the outer contour is circular.

* * * * *